(12) United States Patent
Bezwada

(10) Patent No.: US 8,053,591 B2
(45) Date of Patent: Nov. 8, 2011

(54) FUNCTIONALIZED BIODEGRADABLE TRICLOSAN MONOMERS AND OLIGOMERS FOR CONTROLLED RELEASE

(75) Inventor: Rao S. Bezwada, Hillsborough, NJ (US)

(73) Assignee: Bezwada Biomedical, LLC, Hillsborough, NJ (US)

( * ) Notice: Subject to any disclaimer, the term of this patent is extended or adjusted under 35 U.S.C. 154(b) by 552 days.

(21) Appl. No.: 12/212,233

(22) Filed: Sep. 17, 2008

(65) Prior Publication Data

US 2009/0105352 A1 Apr. 23, 2009

Related U.S. Application Data

(60) Provisional application No. 60/975,374, filed on Sep. 26, 2007.

(51) Int. Cl.
*C07C 69/76* (2006.01)
(52) U.S. Cl. ................................................ 560/61
(58) Field of Classification Search .................. None
See application file for complete search history.

(56) References Cited

U.S. PATENT DOCUMENTS

| | | | |
|---|---|---|---|
| 3,903,007 A * | 9/1975 | Model et al. ................... | 514/548 |
| 3,987,797 A | 10/1976 | Stephenson | |
| 4,020,100 A | 4/1977 | Evans | |
| 4,024,871 A | 5/1977 | Stephenson | |
| 4,829,099 A | 5/1989 | Fuller | |
| 5,378,540 A | 1/1995 | Olson | |
| 5,521,431 A | 5/1996 | Tahara | |
| 5,801,033 A | 9/1998 | Hubbell | |
| 5,834,274 A | 11/1998 | Hubbell | |
| 5,834,513 A | 11/1998 | Ptchelintsev | |
| 5,843,743 A | 12/1998 | Hubbell | |
| 5,932,229 A | 8/1999 | Ptchelintsev | |
| 6,045,813 A | 4/2000 | Ferguson | |
| 6,083,208 A | 7/2000 | Modak | |
| 6,106,505 A | 8/2000 | Modak | |
| 6,207,139 B1 | 3/2001 | Lee | |
| 6,224,579 B1 | 5/2001 | Modak | |
| 6,596,657 B1 | 7/2003 | Shalaby | |
| 6,780,799 B2 | 8/2004 | Shalaby | |
| 6,887,974 B2 | 5/2005 | Pathak | |
| 6,955,827 B2 | 10/2005 | Barabolak | |
| 2002/0028229 A1 | 3/2002 | Lezdey | |
| 2003/0158598 A1 | 8/2003 | Ashton | |
| 2004/0096476 A1 | 5/2004 | Uhrich | |
| 2004/0185250 A1 | 9/2004 | John | |
| 2005/0238689 A1 | 10/2005 | Carpenter | |
| 2005/0267543 A1* | 12/2005 | Heruth et al. ................... | 607/36 |
| 2006/0013851 A1 | 1/2006 | Giroux | |
| 2006/0091034 A1 | 5/2006 | Scalzo | |
| 2006/0172983 A1 | 8/2006 | Bezwada | |
| 2006/0188547 A1 | 8/2006 | Bezwada | |
| 2007/0251831 A1 | 11/2007 | Kaczur | |

FOREIGN PATENT DOCUMENTS

| | | |
|---|---|---|
| EP | 0099177 | 1/1984 |
| EP | 1460089 | 9/2004 |
| WO | WO 9638528 | 12/1996 |
| WO | WO 2004/008101 | 1/2004 |
| WO | WO 2006/052790 | 5/2006 |

OTHER PUBLICATIONS

Silverman (The Organic Chemistry of Drug Design and Drug Action, 1992, Academic Press Inc.).*
Remington's Pharmaceutical Sciences, 18$^{th}$ ed., Mack Publishing Company, Easton, PA, 1990, p. 1445.
van Dijk-Wolthuis, W.N.W.; Hoogeboom, J.; van Steenbergen, M.; Tsang, S.; and Hennick, W. "Degradation and Release Behavior of Dextran-Based Hydrogels", Macromolecules, 30; (1997) 4639-4645.
van Dijk-Wolthuis, W.N.E.; Tsang, S.; Kettenes-van den Bosch, J.; and Hennick, W. "A new class of polymerizable dextrans with hydrolysable groups: hydroxyethyl methacrylated dextran with and without oligolactate spacer", Polymer, 38 (25); (1997) 6235-6242.
Kurisawa et al, Macromol. Chem. Phys. 199, 705-709 (1998).
Heller, J.; Helwing, R.F.; Baker, R.W.; and Tuttle, M.E. "Controlled release of water-soluble macromolecules from bioerodible hydrogels" Biomaterials, 4; (1983) 262-266.
Brondsted (Brondsted, H.; and Kopccek, J. "Hydrogels for site-specific oral drug deliver: synthesis and characterization" Biomaterials, 12; (1991) 584-592.
Ulbrich, K.; Subr, V.; Seymour, L.W.; and Duncan, R. "Novel biodegradable hydrogels prepared using the divinylic crosslinking agent N, O-dimethacryloylhydroxylamine 1. Synthesis and characterization of rates of gel degradation, and rate of release of model drugs, in vitro and in vivo" Journal of Controlled Release, 24; (1993) 181-190.
Gutowska et al, J. Biomater. Res., 29, 811-21 (1995).
Hoffman, J. Controlled Release, 6, 297-305 (1987).
Mikos et al, Biomaterials, 14, 323-329 (1993).
Schugens et al, J. Biomed. Mater. Res., 30, 449-462 (1996).
Bulletin of the Material Research Society, Special Issue on Tissue Engineering (Guest Editor: Joachim Kohn), 21 (11), 22-26 (1996).

* cited by examiner

*Primary Examiner* — Daniel Sullivan
*Assistant Examiner* — Jennifer C Sawyer
(74) *Attorney, Agent, or Firm* — Vance Intellectual Property, PC

(57) ABSTRACT

This invention relates to the discovery of functionalized triclosan monomers and oligomers that, when incorporated into a substrate of, or applied as part of a coating to, medical devices and/or consumer products may extend the duration of antimicrobial properties to the medical devices and/or consumer products.

24 Claims, No Drawings

FUNCTIONALIZED BIODEGRADABLE TRICLOSAN MONOMERS AND OLIGOMERS FOR CONTROLLED RELEASE

CROSS REFERENCE TO RELATED APPLICATIONS

This application claims the benefit of U.S. Application No. 60/975,374, filed Sep. 26, 2007, the disclosure of which is hereby incorporated herein by reference in its entirety.

FIELD OF THE INVENTION

This invention relates to functionalized triclosan monomers and oligomers that, when incorporated into a substrate of, or applied as part of a coating to, medical devices and/or consumer products may extend the duration of antimicrobial properties to the medical devices and/or consumer products.

BACKGROUND OF THE INVENTION

Triclosan is a chlorinated aromatic compound that has ether and phenol groups. Such phenols reportedly often show anti-bacterial properties. Triclosan may be used in soaps, deodorants, toothpastes mouthwashes, and cleaning supplies and is incorporated in an increasing number of consumer products, such as kitchen utensils, toys, bedding, socks, and trash bags. It has been reportedly shown as effective in reducing and controlling bacterial contamination on the hands and on treated products. More recently, it has been reported that showering or bathing with 2% triclosan is a recommended regime for the decolonization of patients whose skin is carrying methicillin resistant *Staphylococcus aureus* following the successful control of MRSA outbreaks in several clinical settings.

Triclosan is disclosed as being useful as an antimicrobial agent in various formulations in the following patents: EP1460089; U.S. Pat. No. 6,045,813; U.S. Pat. No. 6,955,827; U.S. Pat. No. 6,224,579; U.S. Pat. No. 6,207,139; U.S. Pat. No. 6,596,657; U.S. Pat. No. 6,780,799; U.S. Pat. No. 3,903,007; U.S. Pat. No. 3,987,797; U.S. Pat. No. 4,024,871; U.S. Pat. No. 5,378,540; U.S. Pat. No. 6,106,505; U.S. Pat. No. 6,083,208; US 2004/0185250; US 2006/0091034; US 2002/0028229; WO 96/38528; U.S. Pat. No. 4,020,100; EA 0099177.

Certain dental products containing triclosan are described in U.S. Pat. No. 6,207,139 that are reported as having anti-tartar activity.

In U.S. Pat. Nos. 6,596,657 and 6,780,799, Shalaby described the use of sodium triclosan salt, reported as being useful to impart antimicrobial characteristics to fabrics.

In U.S. Pat. No. 3,903,007 Model, et al. the use of 2-acyloxy-triclosan was disclosed and reported as being useful for detergent compositions.

In U.S. Pat. Nos. 6,106,505 and 6,083,208, Modak et al. described polymeric medical articles reportedly comprising synergistic combinations of the antiinfective agents chlorhexidine and triclosan.

US patent application 20040185250 discloses certain triclosan-containing absorbable antimicrobial sutures reported having extended antimicrobial properties. Triclosan was reported to be incorporated into the absorbable sutures by coating, soaking, soaking and coating of triclosan containing solutions or adding triclosan into absorbable polymers before they are processed into fibers.

Lezdey et al. (US patent application 20020028229) disclosed antimicrobial compositions that reported contain a phenol complex with a film forming complex of a polycarboxylic acid and a microbicide containing at least two quaternary amine groups.

In US patent application 20060091034, Scalzo et al. described a method for making an antimicrobial suture, disclosed as comprising the steps of positioning an antimicrobial agent source within a package comprising an inner surface, said antimicrobial agent being selected from the group consisting of halogenated hydroxyl ethers, acyloxydiphenyl ethers, and combinations thereof; positioning a medical device within the package; and subjecting the package, the antimicrobial agent source and the medical device to time, temperature and pressure conditions sufficient to vapor transfer an effective amount of the antimicrobial agent from the antimicrobial agent source to the medical device, thereby substantially inhibiting bacterial colonization on the medical device. As an alternative, the disclosure reportedly provided a packaged medical device produced according to the steps of positioning a medical device within a package; exposing the package having the medical device to an antimicrobial agent source; and subjecting the package having the medical device and the antimicrobial agent source to time, temperature and pressure conditions sufficient to transfer an effective amount of the antimicrobial agent from the antimicrobial agent source to the medical device within the package, thereby substantially inhibiting bacterial colonization on the medical device.

While triclosan compounds have various known beneficial uses, they generally are insoluble or partially soluble in water or the human body and are difficult to hydrolyze. They are also very difficult to polymerize in the phenolic state. As such, there are still unmet needs for materials with improved properties, in particular those materials having improved water compatibility, controlled release, targeted release to specific organs, and the like. The present invention is directed to these and other important ends.

SUMMARY OF THE INVENTION

The present invention in part provides hydrolysable functionalized triclosan monomers and oligomers with tunable degradation profile. In certain embodiments, the hydrolytic degradation of monomers and oligomers of the present invention releases triclosan as such with no change in native chemical structure.

Applicants have found that triclosan may be functionalized with safe and biocompatible molecules such as glycolic acid, lactic acid, p-dioxanone, and/or caprolactone monomers. By careful selection of the biocompatible molecules, the hydrolysis profiles of these new functionalized triclosan compounds are more highly controllable. Other compound properties that are favorably affected include increased solubility, improved bioavailability, improved efficacy, and enhanced functionality.

The functionalization of triclosan using biocompatible molecules such as those described herein produces a hydrolysable, bioabsorbable compound. This process enhances the native value of triclosan by providing the resultant compound or combination of compounds with a specific, controlled degradation profile or range, enabling the controlled release of triclosan over an extended, controllable time range. The different controlled release profiles represent slow, moderate and/or rapid release of the active substance (triclosan). In certain embodiments this release may be targeted to one or more specific organs or parts of the body. The invention described herein greatly extends the usefulness of triclosan and provides greater control of the bioavailability of the triclosan while retaining its inherent biological properties.

Because, in certain embodiments, the functionalized triclosan compounds of the present invention retain the innate properties of the active triclosan compound, they may be used, in many instances, in applications wherein triclosan and/or triclosan compounds are typically employed. For example, they may serve as enhanced antimicrobial agents that find use, for example, in controlled release preparations, cosmetic applications, and flavors. They may also be employed, for example, in coatings for biomedical devices, such as stents, absorbable implantable devices, and/or surgical sutures, and/or for biodegradable chewing gum, nutriceuticals, or drug delivery. In addition, the active portion of the functionalized triclosan has improved bioavailability and/or increased solubility. The compounds of the present invention permit the user to better control the degradation and/or target delivery of the active triclosan component. The compounds may be further reacted and, in many cases, further polymerized, expanding their usefulness.

The present invention also relates to the discovery of functionalized triclosan compounds, and the observation that the resultant functionalized triclosan compounds and their oligomers have controllable degradation profiles, releasing the active triclosan component over a desired time range. The compounds may be used alone or in combination with one or more other functionalized triclosan compounds of the invention as a mixture in order to extend the time range over which the active ingredient is released. The compounds may also be used in combination with absorbable polymers to further extend their usefulness by providing still greater variation in, and control of, the degradation or hydrolysis range of the functionalized triclosan compounds in the mixture.

DETAILED DESCRIPTION OF THE INVENTION

In one embodiment, the present invention provides functionalized triclosan oligomers of formulas A, B, and/or C:

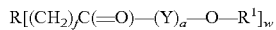

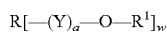

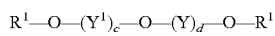

wherein:
each Y is independently:
—OCH$_2$C(=O)— (inverse glycolic ester moiety),
—OCH(CH$_3$)C(=O)— (inverse lactic ester moiety),
—OCH$_2$CH$_2$OCH$_2$C(=O)— (inverse dioxanone ester moiety), —OCH$_2$CH$_2$CH$_2$CH$_2$CH$_2$C(=O)— (inverse caprolactone ester moiety), —O(CH$_2$)$_y$C(=O)—, or —O(CH$_2$CH$_2$O)$_z$OCH$_2$C(=O)—;

each Y$^1$ is independently:
—C(=O)CH$_2$O— (glycolic ester moiety), —C(=O)CH(CH$_3$)O— (lactic ester moiety), —C(=O)CH$_2$OCH$_2$CH$_2$O— (dioxanone ester moiety), —C(=O)CH$_2$CH$_2$CH$_2$CH$_2$CH$_2$O— (caprolactone ester moiety), —C(=O)(CH$_2$)$_m$O—, or —C(=O)CH$_2$O(CH$_2$CH$_2$O)$_n$—;

R is a di-, tri, tetra-, penta- or hexaradical derived from C$_{1-25}$ alkyl, aryl, or aryl-(C$_{1-6}$alkyl)$_{1-3}$-, wherein from 1-4 of the CH$_2$ groups within the alkyl chain are optionally independently replaced by O or S atoms, preferably by O atoms, such that each of said O or S atoms is attached only to carbon atoms in the alkyl chain, with the proviso that the O or S atoms are separated from the di-, tri, tetra-, penta- or hexaradical chain ends by at least one carbon atom and that multiple O or S atoms in the di-, tri, tetra-, penta- or hexaradical chain must be separated from each other by at least two carbon atoms; or R is —[CH$_2$CH$_2$O—]$_p$—, wherein p is an integer from about 10 to about 50;

R$^1$ is:

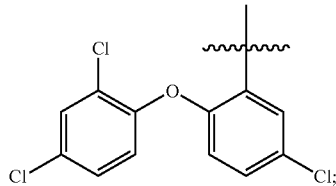

each a is independently an integer from about 1 to about 8;
each f is independently the integer 0 or 1; with the proviso that when f is 0, then R is other than —[CH$_2$CH$_2$O—]$_p$—;
each m and n is independently an integer from about 2 to about 24;
w is an integer from about 2 to about 6; and
c and d are each an integer from 1 to 5, with the proviso that the sum of c+d is an integer from about 2 to about 6.

In certain preferred embodiments of formula B oligomers, and/or medical devices or medical device coatings thereof comprising the oligomers, the functionalized triclosan oligomer has the structure:

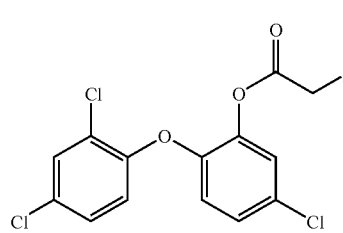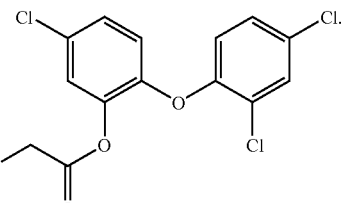

In an embodiment, the present invention provides functionalized triclosan monomers of formula I:

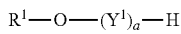
I wherein:

each Y¹ is independently:
—C(=O)CH₂O— (glycolic ester moiety), —C(=O)CH(CH₃)O— (lactic ester moiety), —C(=O)CH₂OCH₂CH₂O— (dioxanone ester moiety), —C(=O)CH₂CH₂CH₂CH₂CH₂O— (caprolactone ester moiety), —C(=O)(CH₂)$_m$O—, or —C(=O)CH₂O(CH₂CH₂O)$_n$—;

R¹ is:

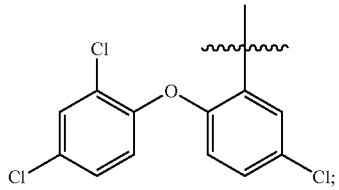

a is an integer from about 1 to about 8; and each m and n is independently an integer from about 2 to about 24.

In an embodiment, the present invention provides functionalized triclosan monomers of formula II:

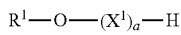
II wherein:

each X¹ is independently:
—CH₂C(=O)O— (glycolic acid moiety), —CH(CH₃)C(=O)O— (lactic acid moiety), —CH₂CH₂OCH₂C(=O)O— (dioxanone moiety), —CH₂CH₂CH₂CH₂CH₂C(=O)O— (caprolactone moiety), —(CH₂)$_y$C(=O)O—, or —(CH₂CH₂O)$_z$CH₂C(=O)O—;

R¹ is:

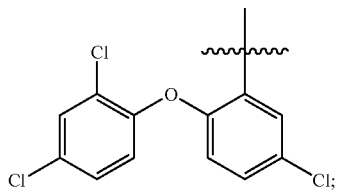

a is an integer from about 1 to about 8; and each y and z is independently an integer from about 2 to about 24.

In certain preferred embodiments of formula II monomers, and/or medical devices or medical device coatings thereof comprising the formula II monomers, the functionalized triclosan monomers are selected from the group consisting of:

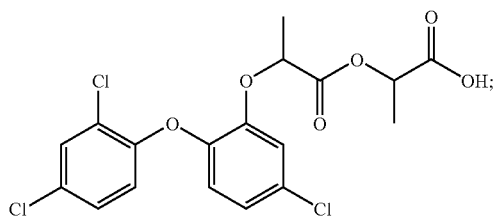

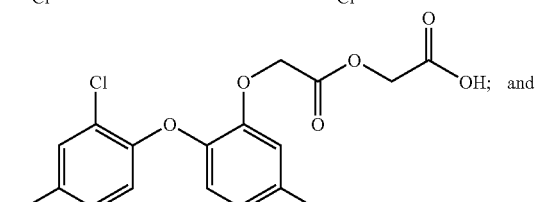

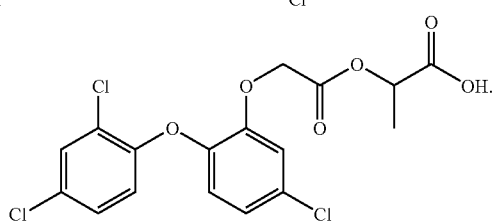

In another embodiment, the present invention provides functionalized triclosan monomers of formula III:

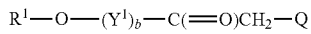
III wherein:

each Y¹ is independently:
—C(=O)CH₂O— (glycolic ester moiety), —C(=O)CH(CH₃)O— (lactic ester moiety), —C(=O)CH₂OCH₂CH₂O— (dioxanone ester moiety), —C(=O)CH₂CH₂CH₂CH₂CH₂O— (caprolactone ester moiety), —C(=O)(CH₂)$_m$O—, or —C(=O)CH₂O(CH₂CH₂O)$_n$—;

R¹ is:

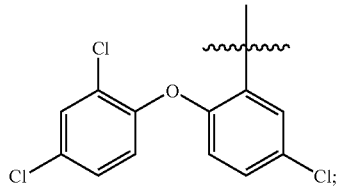

b is an integer from about 1 to about 8;

each m and n is independently an integer from about 2 to about 24; and

Q is F, Cl, Br, or I.

In another embodiment, the present invention provides functionalized triclosan oligomers of formula IV:

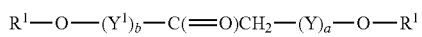
IV wherein:

each Y is independently:
—OCH$_2$C(=O)— (inverse glycolic ester moiety), —OCH(CH$_3$)C(=O)— (inverse lactic ester moiety), —OCH$_2$CH$_2$OCH$_2$C(=O)— (inverse dioxanone ester moiety), —OCH$_2$CH$_2$CH$_2$CH$_2$CH$_2$C(=O)— (inverse caprolactone ester moiety), —O(CH$_2$)$_m$C(=O)—, or —O(CH$_2$CH$_2$O)$_n$OCH$_2$C(=O)—;

each Y$^1$ is independently:
—C(=O)CH$_2$O— (glycolic ester moiety), —C(=O)CH(CH$_3$)O— (lactic ester moiety), —C(=O)CH$_2$OCH$_2$CH$_2$O— (dioxanone ester moiety), —C(=O)CH$_2$CH$_2$CH$_2$CH$_2$CH$_2$O— (caprolactone ester moiety), —C(=O)(CH$_2$)$_m$O—, or —C(=O)CH$_2$O(CH$_2$CH$_2$O)$_n$—;

R$^1$ is:

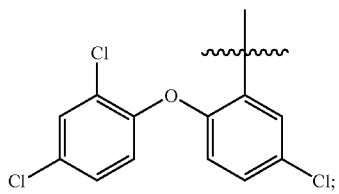

a and b are each independently an integer from about 1 to about 8;

each m and n is independently an integer from about 2 to about 24.

In another embodiment, the present invention provides functionalized triclosan oligomers of formula V:

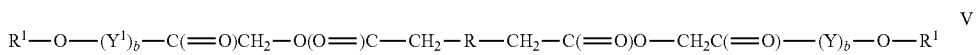

wherein:

each Y is independently:
—OCH$_2$C(=O)— (inverse glycolic ester moiety), —OCH(CH$_3$)C(=O)— (inverse lactic ester moiety), —OCH$_2$CH$_2$OCH$_2$C(=O)— (inverse dioxanone ester moiety), —OCH$_2$CH$_2$CH$_2$CH$_2$CH$_2$C(=O)— (inverse caprolactone ester moiety), —O(CH$_2$)$_m$C(=O)—, or —O(CH$_2$CH$_2$O)$_n$OCH$_2$C(=O)—;

each Y$^1$ is independently:
—C(=O)CH$_2$O— (glycolic ester moiety), —C(=O)CH(CH$_3$)O— (lactic ester moiety), —C(=O)CH$_2$OCH$_2$CH$_2$O— (dioxanone ester moiety), —C(=O)CH$_2$CH$_2$CH$_2$CH$_2$CH$_2$O— (caprolactone ester moiety), —C(=O)(CH$_2$)$_m$O—, or —C(=O)CH$_2$O(CH$_2$CH$_2$O)$_n$—;

R is a diradical derived from C$_{1-25}$ alkyl, aryl, or aryl-(C$_{1-6}$ alkyl)$_{1-3}$-, wherein from 1-4 of the CH$_2$ groups within the alkyl chain are optionally independently replaced by O or S atoms, preferably by O atoms, such that each of said O or S atoms is attached only to carbon atoms in the alkyl chain, with the proviso that the O or S atoms are separated from the diradical chain must be separated from each other by at least two carbon atoms; or R is —[CH$_2$CH$_2$O—]$_p$—, wherein p is an integer from about 10 to about 50;

R$^1$ is:

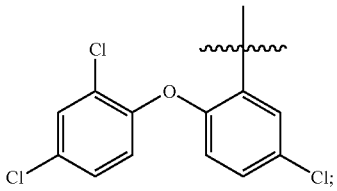

each b is independently an integer from about 0 to about 8; and each m and n is independently an integer from about 2 to about 24.

The oligomers of formula A of the present invention are prepared by reacting monomers of formula I or their halo derivatives (formula III, wherein b is (a−1) and Q is halo) with linear and/or multi-armed acids of formula R—(C(=O)OH)$_s$, wherein s is an integer from about 2 to about 6 and where the acids used maybe symmetrical or unsymmetrical, preferably symmetrical or unsymmetrical ether diacids (e.g., see structures below). Oligomers of formula V are, for example, prepared by reacting monomers of formula III with linear or non-linear, symmetrical or non-symmetrical diacids of formula R—(C(=O)OH)$_s$, wherein s is the integer 2.

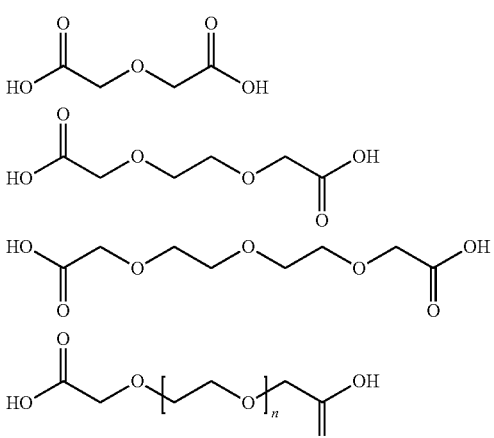

n = 10-50

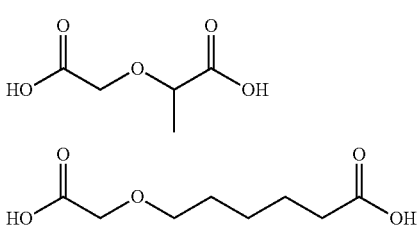

-continued

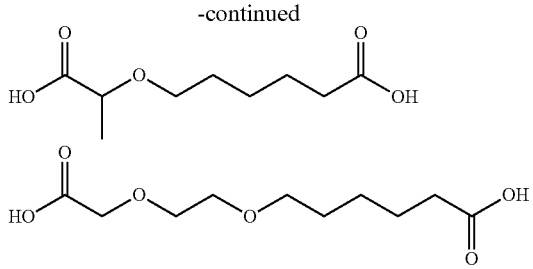

In another embodiment, the present invention provides functionalized triclosan oligomers of formula VI:

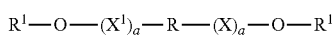

wherein:
each X is independently:
—OC(=O)CH$_2$— (inverse glycolic acid moiety), —OC(=O)CH(CH$_3$)— (inverse lactic acid moiety), —OC(=O)CH$_2$OCH$_2$CH$_2$— (inverse dioxanone acid moiety), —OC(=O)CH$_2$CH$_2$CH$_2$CH$_2$CH$_2$— (inverse caprolactone acid moiety), —OC(=O)(CH$_2$)$_y$—, or —OC(=O)CH$_2$(OCH$_2$CH$_2$)$_z$—.
each X$^1$ is independently:
—CH$_2$C(=O)O— (glycolic acid moiety), —CH(CH$_3$)C(=O)O— (lactic acid moiety), —CH$_2$CH$_2$OCH$_2$C(=O)O— (dioxanone moiety), —CH$_2$CH$_2$CH$_2$CH$_2$CH$_2$C(=O)O— (caprolactone moiety), —(CH$_2$)$_y$C(=O)O—, or —(CH$_2$CH$_2$O)$_z$CH$_2$C(=O)O—;
R is a diradical derived from C$_{1-25}$ alkyl, aryl, or aryl-(C$_{1-6}$ alkyl)$_{1-3}$-, wherein from 1-4 of the CH$_2$ groups within the alkyl chain are optionally independently replaced by O or S atoms, preferably by O atoms, such that each of said O or S atoms is attached only to carbon atoms in the alkyl chain, with the proviso that the O or S atoms are separated from the diradical chain ends by at least one carbon atom and that multiple O or S atoms in the diradical chain must be separated from each other by at least two carbon atoms; or R is —[CH$_2$CH$_2$O—]$_p$—, wherein p is an integer from about 10 to about 50; or R is a homopolymer or copolymer of glycolide, lactide, caprolactone, p-dioxanone, or a combination thereof (e.g., M$_n$ of from 100, 200, 300, 400, 500, 600, 700, 800, 900, to 1000);
R$^1$ is:

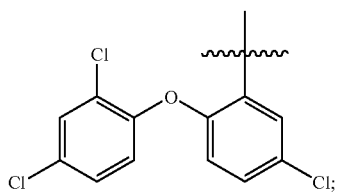

each a is independently an integer from about 0 to about 8; and
each y and z is independently an integer from about 2 to about 24;
with the proviso that when R is a diradical derived from C$_{1-25}$ alkyl, aryl, or aryl-(C$_{1-6}$alkyl)$_{1-3}$-, wherein none of the CH$_2$ groups within the alkyl chain are replaced by O or S atoms, then at least one of a is an integer from about 1 to about 8.

In another embodiment, the present invention provides functionalized triclosan monomers of formula VII:

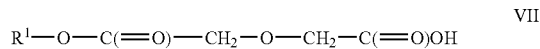

wherein:
R$^1$ is:

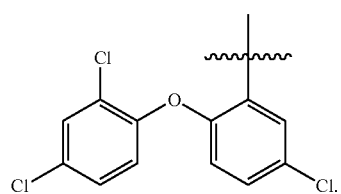

In another embodiment, the present invention provides functionalized triclosan oligomers of formula VIII:

wherein:
Z is selected from —CH$_2$—CH$_2$—, —CH$_2$—O—CH$_2$—, and —CH$_2$—; and
R$^1$ is:

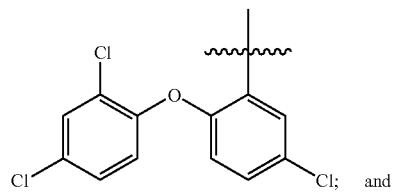

R is a diradical derived from C$_{1-25}$ alkyl, aryl, or aryl-(C$_{1-6}$ alkyl)$_{1-3}$-, wherein from 1-4 of the CH$_2$ groups within the alkyl chain are optionally independently replaced by O or S atoms, preferably by O atoms, such that each of said O or S atoms is attached only to carbon atoms in the alkyl chain, with the proviso that multiple heteroatoms must be separated from each other by at least two carbon atoms and from the diradical chain ends by at least one carbon atom; or R is —[CH$_2$CH$_2$O—]$_p$—, wherein p is an integer from about 10 to about 50;
with the proviso that at least one of Z is —CH$_2$—O—CH$_2$—.

As used herein for functionalized triclosan oligomers of formula VIII, when R is —[CH$_2$CH$_2$O—]$_p$—, the two oxygen atoms in the moiety "O—R—O" are implicit in the R moiety. For example, the terminal oxygen atoms in the diradical —O—CH$_2$CH$_2$—O—CH$_2$CH$_2$—O— (that is, wherein R is —[CH$_2$CH$_2$O—]$_p$— and p is 2) form part of both the R and the two "O" atom functions. Thus when R is R is —[CH$_2$CH$_2$O—]$_p$— and p is 2) the oligomer of formula VIII has the formula:

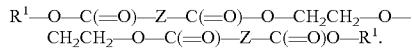

R$^1$—O—C(=O)—Z—C(=O)—O—CH$_2$CH$_2$—O—CH$_2$CH$_2$—O—C(=O)—Z—C(=O)O—R$^1$.

The triclosan-functionalized oligomers of general formula R[OC(=O)—Z—C(=O)O—R$^1$]$_f$ are prepared, for example, by reaction of triclosan-functionalized monomers of formula VII with a linear or multiarmed polyol of general formula R—(OH)$_f$ where f is an integer from about 2 to about 6. In particular, triclosan-functionalized oligomers of formula VIII of the present invention are prepared by reaction of triclosan-functionalized monomers of formula VII with a linear on nonlinear, symmetrical or non-symmetrical diol (f is the integer 2).

In another embodiment, the present invention provides functionalized triclosan oligomers of formula IX:

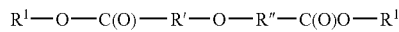

R$^1$—O—C(O)—R'—O—R"—C(O)O—R$^1$     IX wherein:
R' and R" are each independently R is a diradical derived from C$_{1-25}$ alkyl, aryl, or aryl-(C$_{1-6}$alkyl)$_{1-3}$-, wherein from 1-4 of the CH$_2$ groups within the alkyl chain are optionally independently replaced by O or S atoms, preferably by O atoms, such that each of said O or S atoms is attached only to carbon atoms in the alkyl chain, with the proviso that multiple heteroatoms must be separated from each other by at least two carbon atoms and from the diradical chain ends by at least one carbon atom; or R is —[CH$_2$CH$_2$O—]$_p$—, wherein p is an integer from about 10 to about 50; and R$^1$ is:

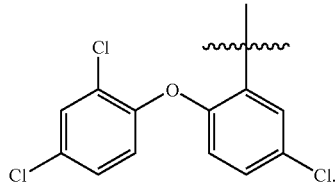

In some embodiments, the invention is directed di-, tri-, or polyamido compounds that are the reaction products of functionalized triclosan oligomers of formula VII:

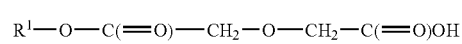

R$^1$—O—C(=O)—CH$_2$—O—CH$_2$—C(=O)OH     VII wherein:
R$^1$ is:

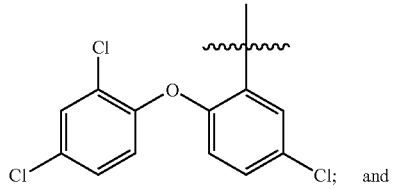  and biodegradable di- tri-, or polyamines.

In certain preferred embodiments of the di-, tri-, or polyamido compounds, the biodegradable di- tri-, or polyamine is selected from the group consisting of:

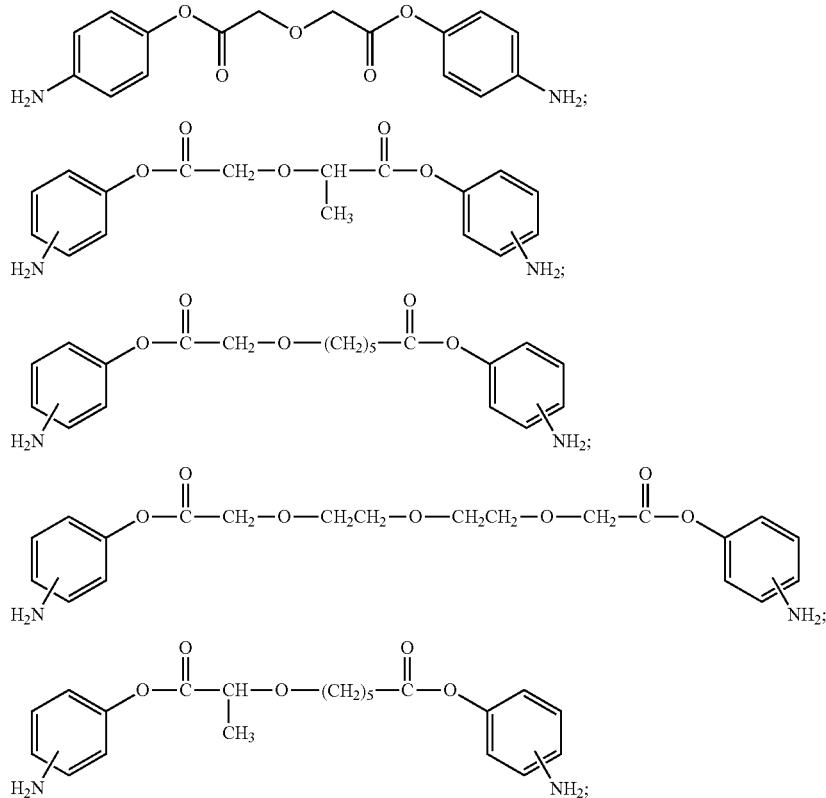

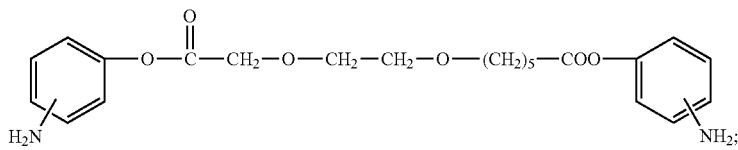
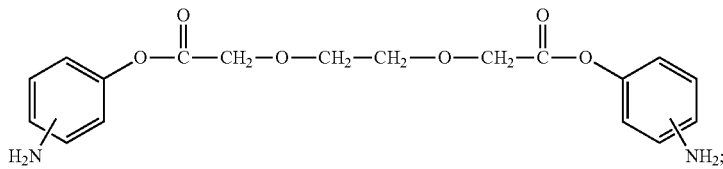
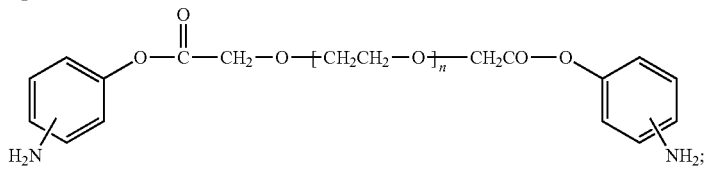
wherein n is an integer from about 10 to about 50;
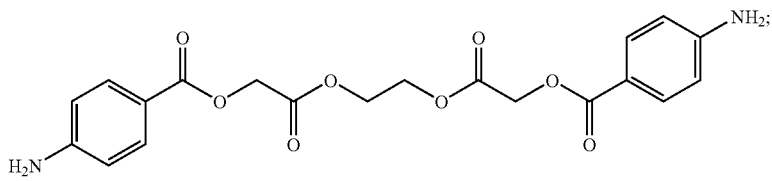
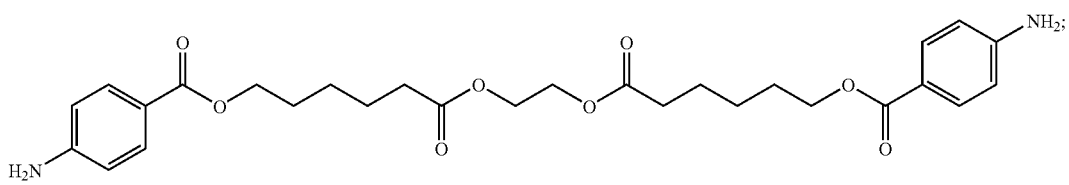
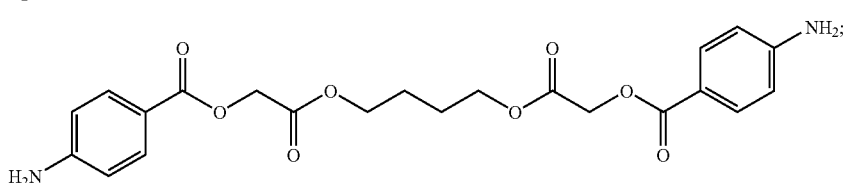
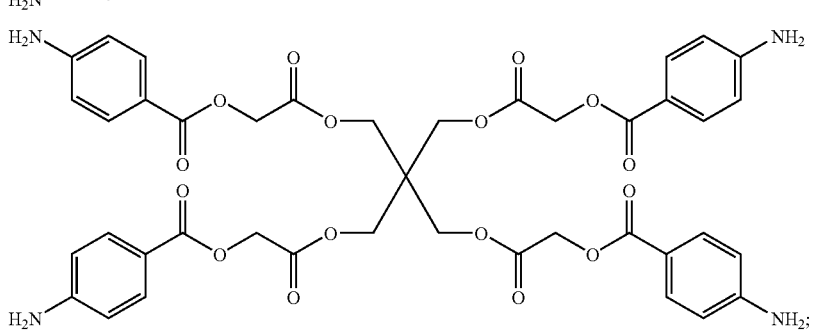
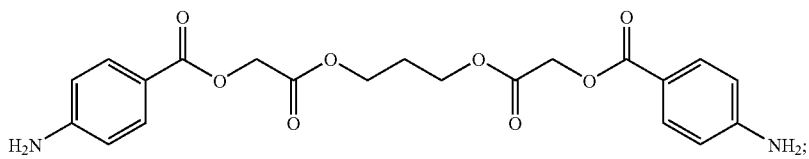

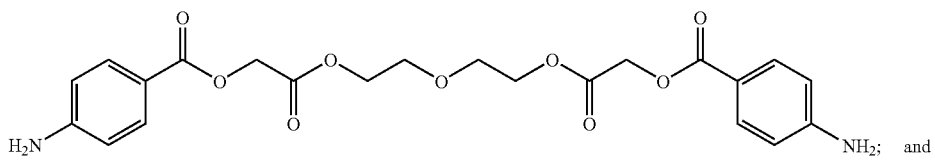
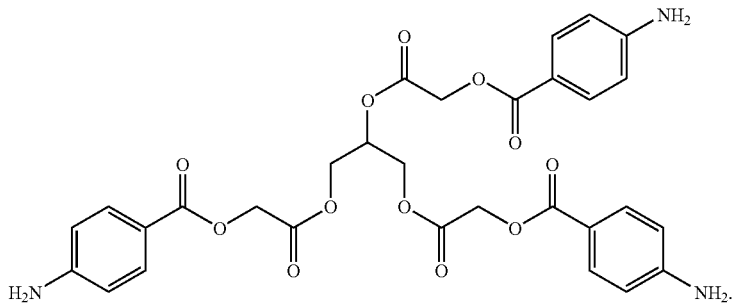
Other embodiments of the present invention are directed to di-, tri-, or polyamido compounds that are the reaction product of a diacid selected from the group consisting of:
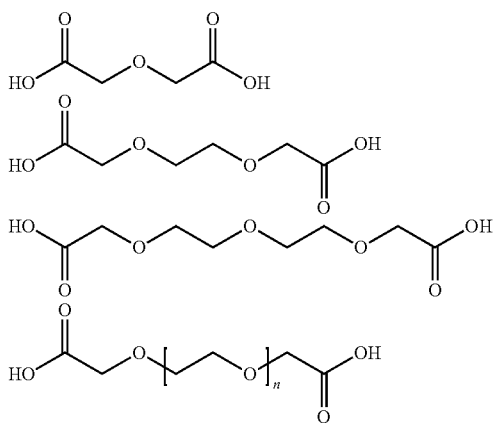
n = 10-50
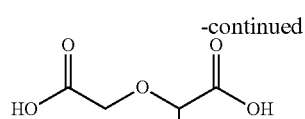
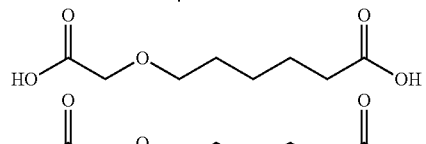
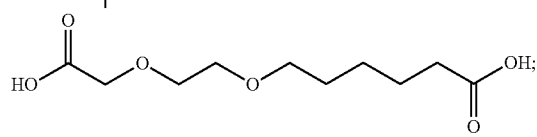
and
a di- tri-, or polyamine is selected from the group consisting of:
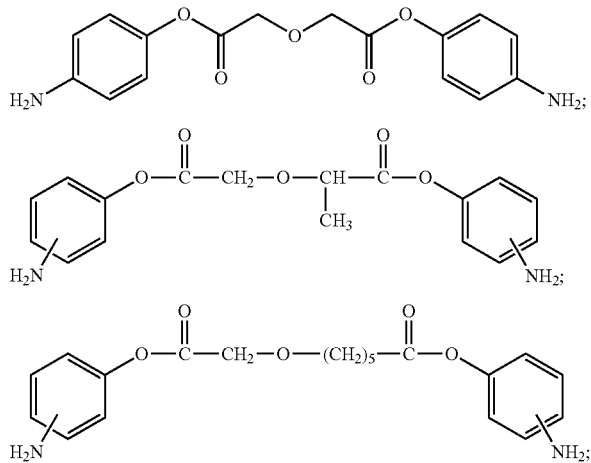

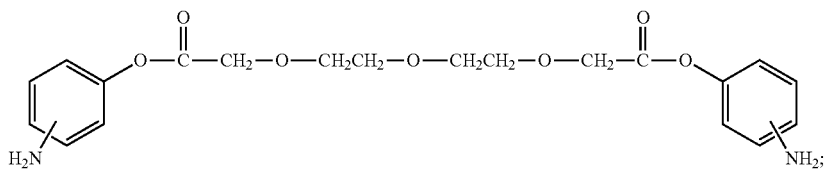
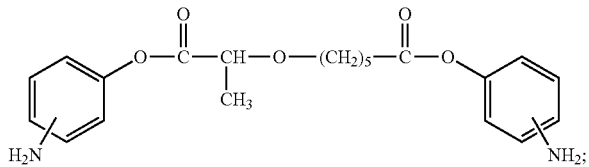
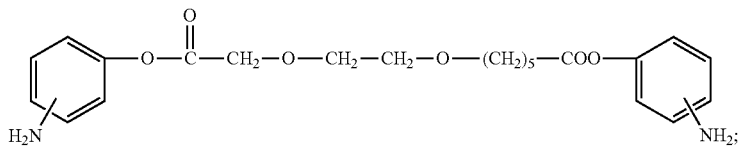
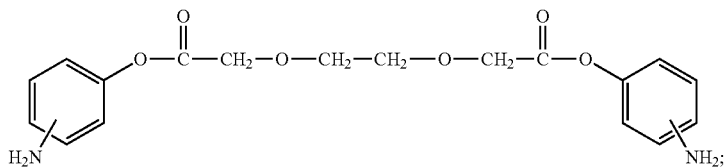
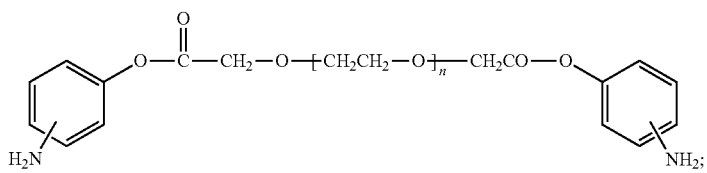
wherein n is an integer from about 10 to about 50;
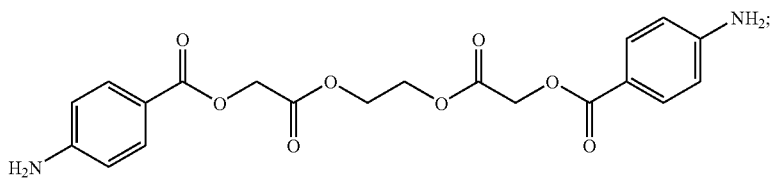
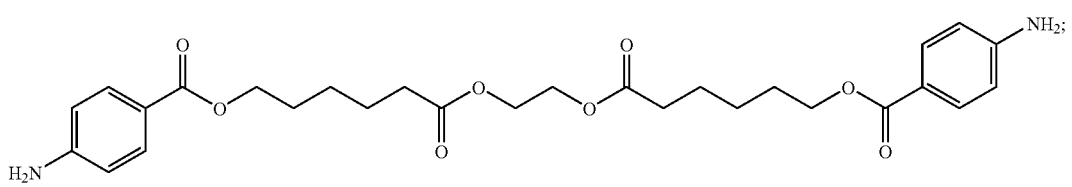
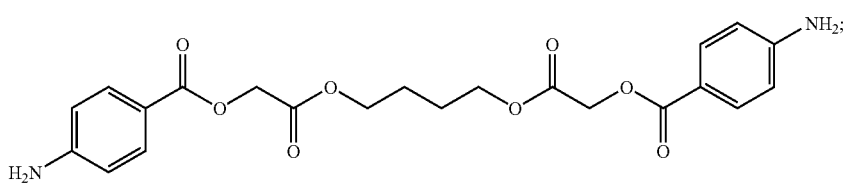

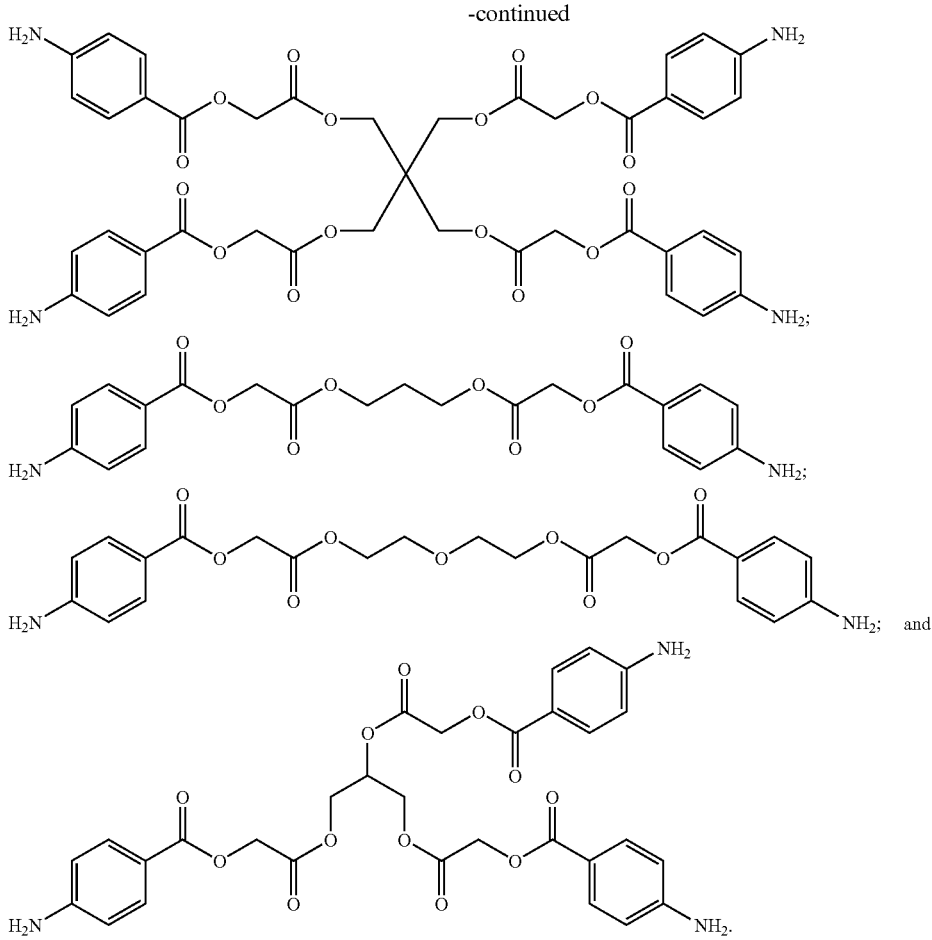

Certain embodiments of the present invention are directed to compositions comprising:

1) a functionalized triclosan monomer of formula III:

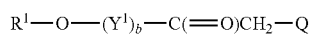

wherein:
each $Y^1$ is independently:
—C(=O)CH$_2$O— (glycolic ester moiety), —C(=O)CH(CH$_3$)O— (lactic ester moiety), —C(=O)CH$_2$OCH$_2$CH$_2$O— (dioxanone ester moiety), —C(=O)CH$_2$CH$_2$CH$_2$CH$_2$CH$_2$O— (caprolactone ester moiety), —C(=O)(CH$_2$)$_m$O—, or —C(=O)CH$_2$O(CH$_2$CH$_2$O)$_n$—;

$R^1$ is:

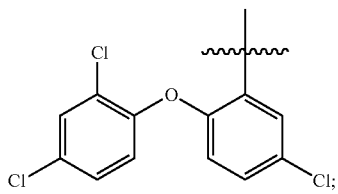

b is an integer from about 1 to about 8;
each m and n is independently an integer from about 2 to about 24; and
Q is F, Cl, Br, or I; and 2) an amine acid selected from the group consisting of:

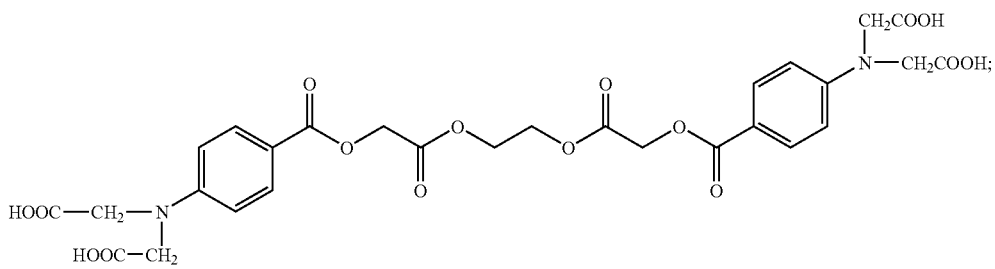

-continued
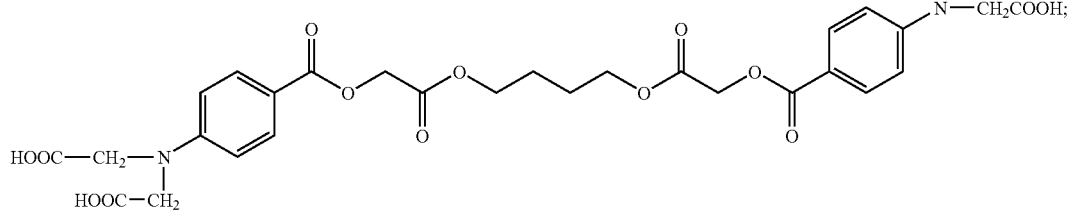
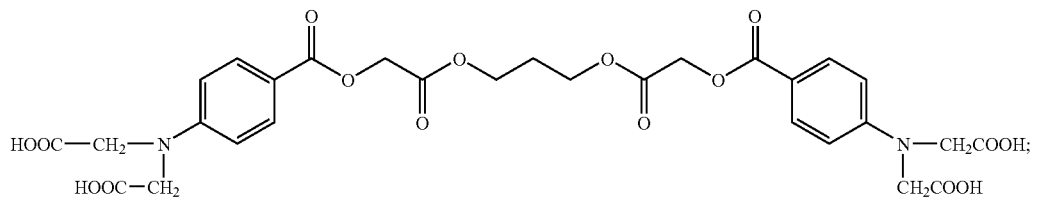
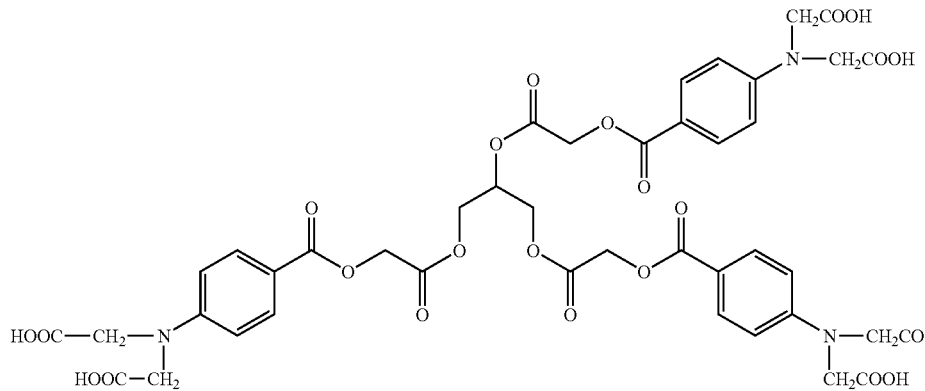
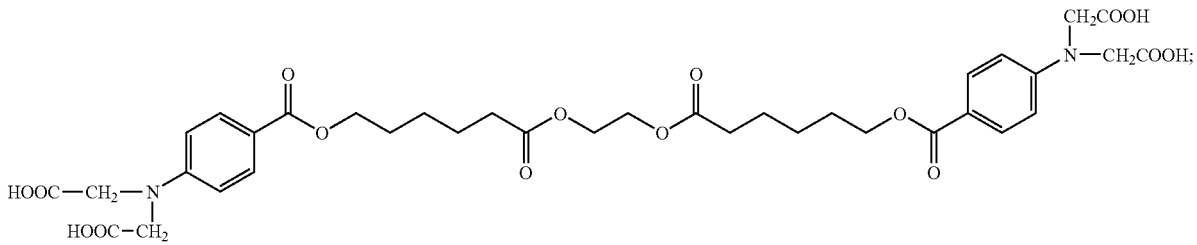
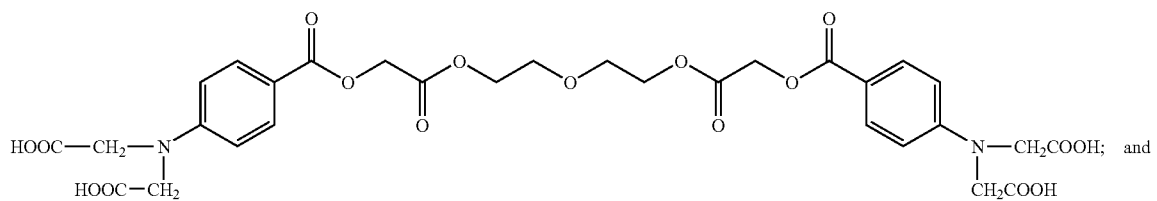; and
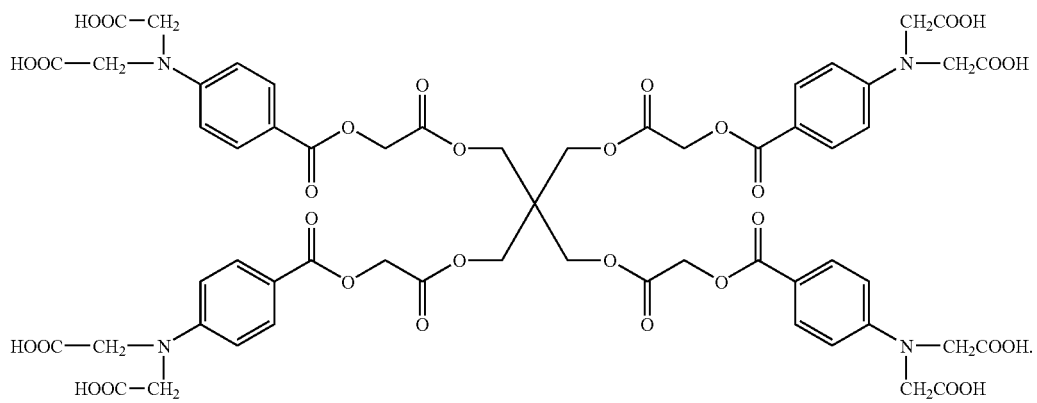

In certain embodiments of the compositions of the present invention, the amine acids are associated with, coordinated to, and/or complexed with the monomers of formula III. In other embodiments, the monomers of formula III react with amine acids to form the corresponding ammonium salt.

In functionalized triclosan monomers and/or oligomers of formula C, the O between the two Y groups depicted as $(Y)-O-(Y^1)$ represents an ether linkage between the Y and $Y^1$ groups such that there is only one —O— ether moiety in the chain $(Y)-O-(Y^1)$. By way of example, when Y is corresponds to —C(=O)CH$_2$O— (glycolic ester moiety), and $Y^1$ corresponds to —OCH(CH$_3$)C(=O)— (inverse lactic ester moiety), the resultant $(Y)-O-(Y^1)$ is —COCH$_2$O—CH(CH$_3$)C(=O)—. Similarly, when R is —[CH$_2$CH$_2$O—]$_p$— and is connected to $(Y^1)$, the resultant R—$(Y^1)$ is —[CH$_2$CH$_2$O—]$_p$—CH(CH$_3$)C(=O)—, when for example, $(Y^1)$ is —OCH(CH$_3$)C(=O)—. When R is —[CH$_2$CH$_2$O—]$_p$—, p is 3, and X is —OC(=O)CH$_2$— and R is attached to X in the following manner (R—X), the resultant R—X may be depicted as —O—[CH$_2$CH$_2$—O—CH$_2$CH$_2$—O—CH$_2$CH$_2$—O]—C(=O)CH$_2$—.

As used herein the term "—[CH$_2$CH$_2$O—]$_p$—" refers to an oligoethyleneoxy diradical moiety, with the understanding that both ends of the diradical bear an oxygen atom. For example, when R is —[CH$_2$CH$_2$O—]$_p$— and p is 3, the diradical R maybe depicted as —O—[CH$_2$CH$_2$—O—CH$_2$CH$_2$—O—CH$_2$CH$_2$—O]—.

In some preferred embodiments of functionalized triclosan monomers and/or oligomers of formula IV, V, or C, Y and $Y^1$ are derived from different hydroxyacid or lactone precursors. As non-limiting examples, Y may be —C(=O)CH$_2$O— (derived from glycolic acid) is and $Y^1$ may be —OCH(CH$_3$)C(=O)— (derived from lactic acid), or Y may be derived from lactic acid and $Y^1$ may be derived from caprolactone.

In some preferred embodiments of functionalized triclosan monomers and/or oligomers of formula VI, X and $X^1$ are derived from different hydroxyacid or lactone precursors. As non-limiting examples, X may be —CH$_2$C(=O)O— (derived from glycolic acid) and $X^1$ may be —OC(=O)CH(CH$_3$)— (derived from lactic acid), or X may be derived from lactic acid and $X^1$ may be derived from caprolactone.

In other preferred embodiments of functionalized triclosan monomers and/or oligomers of formulas V, VI, VIII, A, or B, R is selected from a $C_{2-12}$ alkyl, phenyl, and phenyl-$(C_{1-6}$ alkyl)$_{1-3}$-. In certain preferred embodiments wherein R is alkyl or aryl-$(C_{1-6}$ alkyl)$_{1-3}$-, 1-4 of the CH$_2$ groups within the alkyl or aryl-$(C_{1-6}$alkyl)$_{1-3}$-chain are optionally independently replaced by O or S moieties, such that each of said O or S moieties is attached only to carbon atoms in the alkyl chain, or alternatively, in moieties to at least one alkyl chain carbon atom, the other being either an aryl ring carbon atom or a second alkyl chain carbon atom. In some preferred embodiments, multiple heteroatoms must be separated from each other by at least two carbon atoms and from the di-, tri, tetra-, penta- or hexaradical chain ends by at least one carbon atom;

Alternatively in some preferred embodiments, when R is alkyl, it is more preferably (CH$_2$), (CH$_2$)$_3$, CH(CH$_2$)$_3$, C(CH$_2$)$_4$, or C(CH$_2$CH$_3$)(CH$_2$)$_3$. In still other preferred embodiments, R is (CH$_2$)$_3$, and wherein the C-2 CH$_2$ group within the (CH$_2$)$_3$ chain is optionally replaced by an O moiety. In yet other preferred embodiments, R is (CH$_2$)$_2$, (CH$_2$)$_3$, (CH$_2$)$_4$, (CH$_2$OCH$_2$), or (CH$_2$CH$_2$OCH$_2$CH$_2$). In still other preferred embodiments, R is (CH$_2$CHCH$_2$) when w is 3, or (C(CH$_2$)$_4$) when w is 4.

In other preferred embodiments of functionalized triclosan monomers and/or oligomers of formula IX, R' and R" are each independently $C_{2-12}$ alkyl, phenyl, and phenyl-$(C_{1-6}$ alkyl)$_{1-3}$-. In certain preferred embodiments wherein R is alkyl or aryl-$(C_{1-6}$ alkyl)$_{1-3}$-, 0-3 of the CH$_2$ groups within the alkyl chain are optionally independently replaced by O or S moieties, such that each of said O or S moieties is attached only to carbon atoms in the alkyl chain. Alternatively in some preferred embodiments, when R is alkyl, it is more preferably (CH$_2$), (CH$_2$)$_3$, CH(CH$_2$)$_3$, C(CH$_2$)$_4$, or C(CH$_2$CH$_3$)(CH$_2$)$_3$. In still other preferred embodiments, R is (CH$_2$)$_3$, and wherein the C-2 CH$_2$ group within the (CH$_2$)$_3$ chain is optionally replaced by an O moiety. In yet other preferred embodiments, R is (CH$_2$)$_2$, (CH$_2$)$_3$, (CH$_2$)$_4$, (CH$_2$OCH$_2$), or (CH$_2$CH$_2$OCH$_2$CH$_2$). In still other preferred embodiments, R is (CH$_2$CHCH$_2$) when w is 3, or (C(CH$_2$)$_4$) when w is 4.

In some other preferred embodiments of functionalized triclosan monomers and/or oligomers of formulas I, II, IV, VI, A, or B, each a is independently an integer from about 0 to about 3, more preferably from about 1 to about 3.

In some embodiments of the invention, each a is independently an integer from about 0 to about 8. In certain preferred embodiments at least one a is an integer from about 1 to about 8, more preferably about 2 to about 8. Alternatively preferred, each a is an integer from about 1 to about 8.

In some other preferred embodiments of functionalized triclosan monomers and/or oligomers of formulas III, IV, or V, each b is independently an integer from about 0 to about 3, more preferably from about 1 to about 3.

In some embodiments of the invention, each b is independently an integer from about 0 to about 8. In certain preferred embodiments at least one b is an integer from about 1 to about 8, more preferably about 2 to about 8. Alternatively preferred, each b is an integer from about 1 to about 8.

In certain other preferred embodiments of oligomers or pharmaceutically acceptable salts thereof of formulas A or B, w is an integer from about 2 to about 4.

In still other preferred embodiments functionalized triclosan monomers and/or oligomers of formula II or VI, each X is independently —OC(=O)CH$_2$—, —OC(=O)CH(CH$_3$)—, —OC(=O)CH$_2$OCH$_2$CH$_2$—, or —OC(=O)CH$_2$CH$_2$CH$_2$CH$_2$CH$_2$—; more preferably —OC(=O)CH$_2$— or —OC(=O)CH(CH$_3$)—.

In some other preferred embodiments of functionalized triclosan monomers and/or oligomers of formula VI, each $X^1$ is independently —CH$_2$C(=O)O—, —CH(CH$_3$)C(=O)O—, —CH$_2$CH$_2$OCH$_2$C(=O)O—, or —CH$_2$CH$_2$CH$_2$CH$_2$CH$_2$C(=O)O—, more preferably —CH$_2$C(=O)O— or —CH(CH$_3$)C(=O)O—.

In some preferred embodiments of functionalized triclosan monomers and/or oligomers of formulas I, III, IV, V, A, B, or C, each Y is independently —OCH$_2$C(=O)—, —OCH(CH$_3$)C(=O)—, —OCH$_2$CH$_2$OCH$_2$C(=O)—, or —OCH$_2$CH$_2$CH$_2$CH$_2$CH$_2$C(=O)—, more preferably —OCH$_2$C(=O)— or —OCH(CH$_3$)C(=O)—.

In certain preferred embodiments of oligomers or pharmaceutically acceptable salts thereof of formula IV, V, or C, each $Y^1$ is independently —C(=O)CH$_2$O—, —C(=O)CH(CH$_3$)O—, —C(=O)CH$_2$OCH$_2$CH$_2$O—, or —C(=O)CH$_2$CH$_2$CH$_2$CH$_2$CH$_2$O—; more preferably —C(=O)CH$_2$O— or —C(=O)CH(CH$_3$)O—.

In other preferred embodiments of functionalized triclosan monomers and/or oligomers of formula III, Q is preferably Cl, Br, or I, more preferably Cl or Br, with Cl being even more preferred.

In certain other preferred embodiments of functionalized triclosan monomers and/or oligomers of formula C or F, c and d are each 1, 2, or 3; more preferably both c and d are 1, or they are both 2, or they are both 3.

Examples of linear and branched biologically active and biologically non-active amines that may be useful in the present invention include jeffamines, spermidine, spermine, and putrescine as well as biodegradable amines including but not limited to those shown in FIG. 1 below.

FIG. 1. Some examples of biodegradable amines that maybe used in the present invention
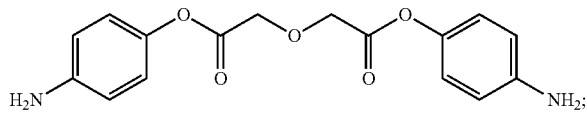
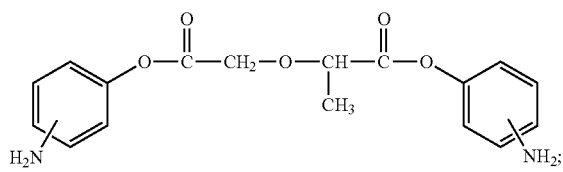
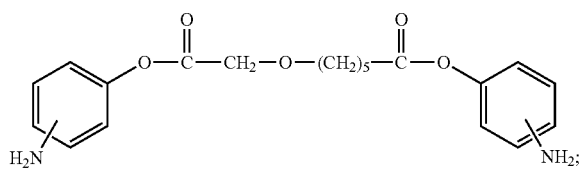
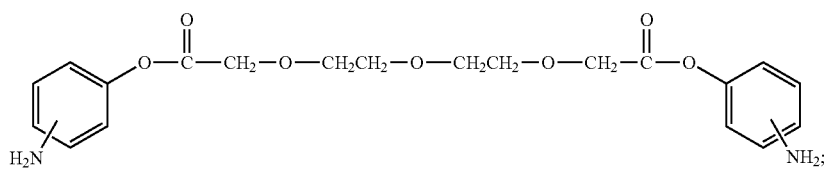
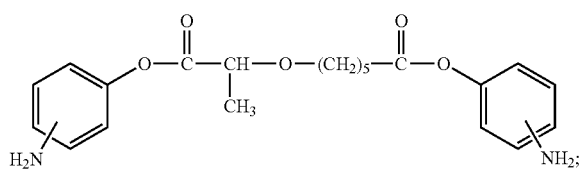
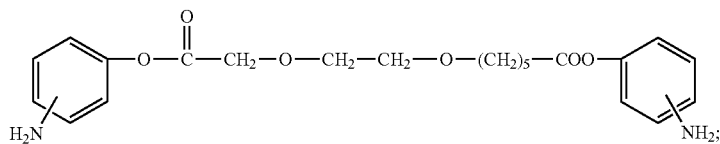
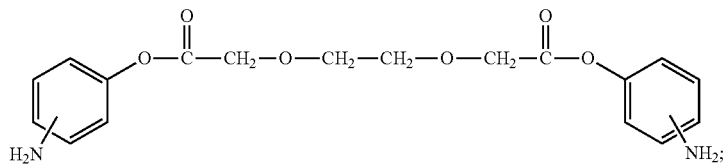
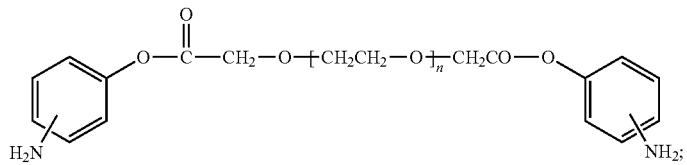
wherein n is an integer from about 10 to about 50;
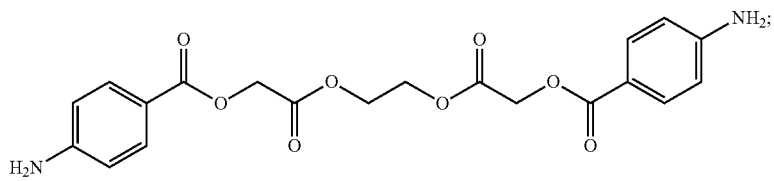

-continued
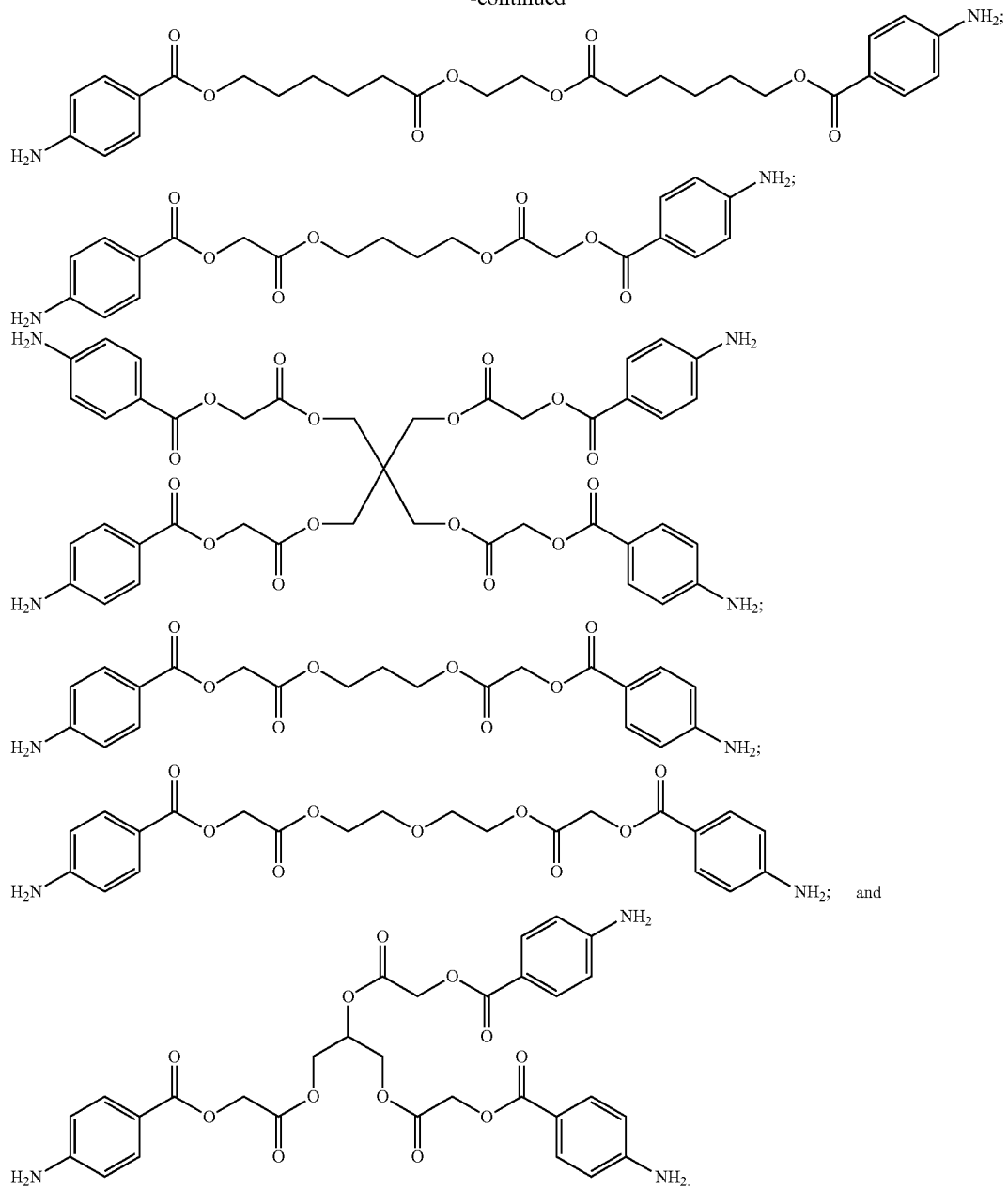
Examples of linear and branched amine acids include but are not limited to those shown in FIG. 2.
FIG. 2. Some examples of amine acids that maybe used in the present invention
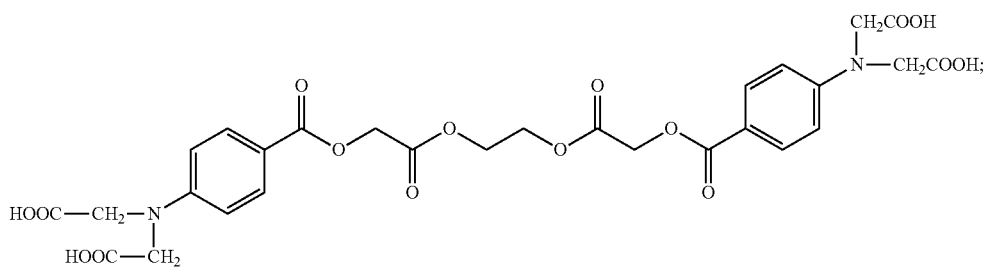

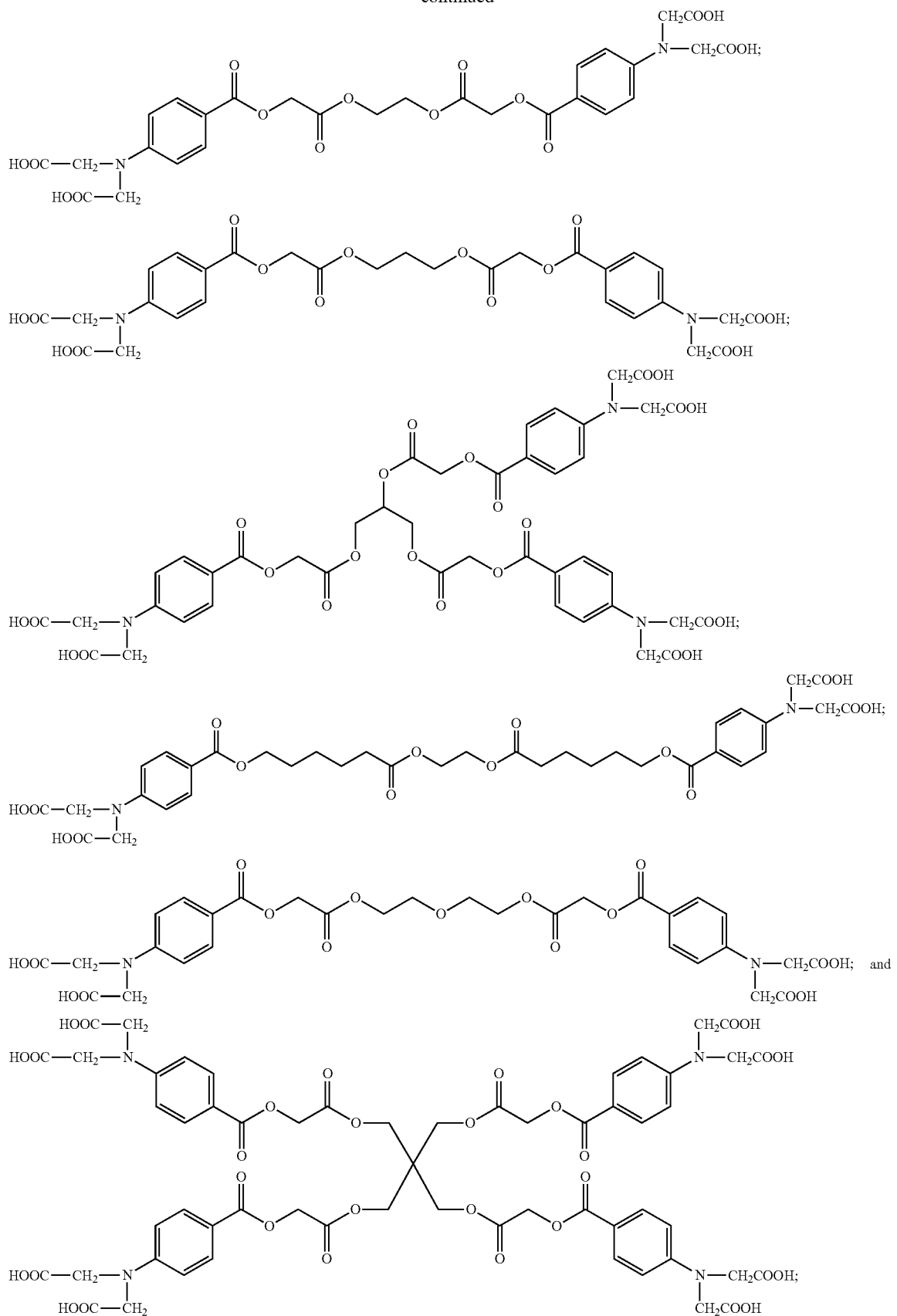

In other embodiments, the present invention provides polymers containing pendant functionalized triclosan groups. These polymers may be obtained, for example, by reaction of functionalized triclosan monomers of formula III of the present invention with linear and branched polymers having pendant acid groups such as polyacrylic acid and polymethacrylic acid by displacement of the moiety Q in formula III monomers by the carboxylate functionality of the polymers having pendant acid groups.

In other embodiments, the present invention provides modified biologically active compounds formed by reacting a biologically active substance (e.g., a drug) containing at least one OH, $CO_2H$, or amine group (e.g., $NH_2$ or tertiary amine) with a functionalized triclosan monomer of Formula II or III. In certain embodiments, the biologically active substances compounds are associated with, coordinated to, and/or complexed with the monomers of formula III. In other embodiments, the monomer of formula III reacts with the biologically active substance to form a covalent bond between the two moieties, such as an ester, ether or amide bond, for example.

In other embodiments, the present invention provides oligomeric quaternary ammonium compounds. These compounds may be obtained, for example, by reaction of functionalized triclosan monomers of formula III of the present invention with tertiary amine-containing biologically active substances, such as Lidocaine and Lidofenin, through displacement of the moiety Q in formula III monomers by the amine functionality of the tertiary amine-containing biologically active substances.

Examples of biologically active compounds useful in certain embodiments include phenolic compounds such as phenols and/or naphthols, indoles, acetophenones, benzophenones, coumarins, furanocoumarins, alkaloids, catechins, chromones, chalcones, flavonoids or bioflavonoids, isoflavones, drugs containing phenolic groups, and/or natural products containing phenolic groups.

Examples of biologically active dihydroxy compound that maybe used to prepare a polymer of the present invention include Adrenalone, Alfuzosin, Alibendol, Amrubicin, Apomorphine, Bamethan, Benzquinamide, Bevantolol, Bifluranol, Bisacodyl, Brodimoprim, Bunazosin, Bupheniode, Carbidopa, Carbuterol, Cyclofenil, Cyclovalone, Daunorubicin, Dichlorophen, Dienestrol, Diethylstilbestrol, Dimestrol, Dithranol, Donepezil, Doxefazepam, Doxorubicin, Entacapone, Epinepheine, Epirubicin, Esomeprazole, Etamivan, Etamsylate, Etilefrine, Ezetimibe, Fenticlor, Fluorescein, Folescutol, Formoterol, Gefitinib, Hexestrol, Hexylresorcinol, Hydroxyethyl salicylate, Ifenprodil, Isoetarine, Isoxsuprine, Itopride, HCl, Khellin, Labetalol, Mitoxantrone, Morclofone, Moxaverine, Normolaxol, Omeprazole, Oxilofrine, Oxepertine, Phenacaine, Phenolphthalein, Prazosin, Tolcapone, Vesnarinone, and Vetradutine.

Examples of biologically active hydroxy/amino compounds that may be used to prepare a polymer of the present invention include Amisulpride, Amodiaquine, Amosulalol, Amoxicillin, Amsacrine, Azacyclonol, Bromopride, Carvedilol, Cefprozil, Cinitapride, Clebopride, Clenbuterol, Ethoxzolamide, Nadoxolol, D-Norpseudoephedrine, and paracetamol.

Examples of biologically active dicarboxylic acid compounds that may be used to prepare a polymer of the present invention include Adipiodone, Cromoglicic acid, Eprosartan, Iocarmic acid, Iodoxamic acid, Ioglycamic acid, Iotroxic acid, Nedocromil.

Examples of biologically active hydroxy/carboxylic acid compounds that may be used to prepare a polymer of the present invention include Acemetacin, Bentiromide, Cinmetacin, Clometacin, Diflunisal, Fendosal, Indometacin, Iophenoic acid, Naproxen, Repaglinide, Salazosulfapyridine, Salicylic Acid, Salsalate, and Sarpogrelate.

Examples of biologically active hydroxyl-acids that may be useful in the present invention include but not limited to 4-hydroxycinnamic acid, Caffeic acid, Chlorogenic acid, Ferulic acid, Sinapinic acid, Vanillic acid, Acemetacin, Bentiromide, Cinmetacin, Clometacin, Diflunisal, Fendosal, Indometacin, Iophenoic acid, Naproxen, Repaglinide, Salazosulfapyridine, Salicylic Acid, Salsalate, and Sarpogrelate.

Examples of biologically active amino/carboxylic acid compounds that may be used to prepare a polymer of the present invention include Aceclofenac, Acediasulfone, Alminoprofen, Amlexanox, Anileridine, Baccofen, Balsalazide sodium, Benzocaine, Bumetanide, Carprofen, Carzenide, Diclofenac, Flufenamic acid, Furosemide, Iobenzamic acid, Iocetamic acid, and Mefenamic acid.

Some structures of biologically active compounds bearing hydroxyl functional groups useful in present invention are shown below in FIG. 3.

FIG. 3.

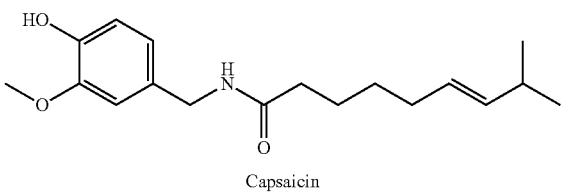

Capsaicin

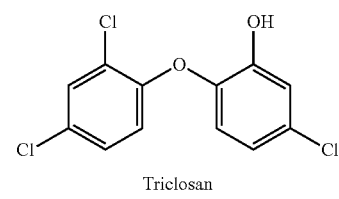

Triclosan

Benzarone

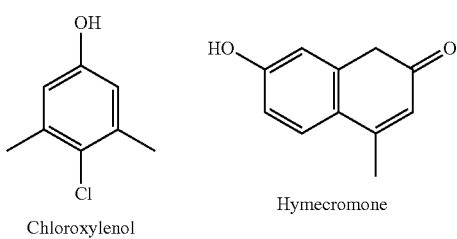

Chloroxylenol

Hymecromone

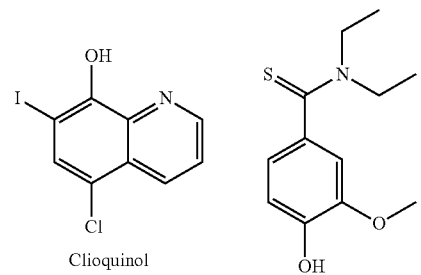

Clioquinol

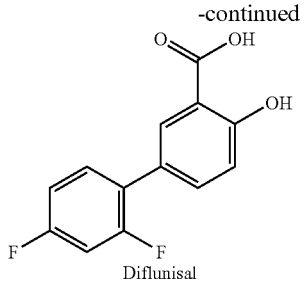

Etamivan

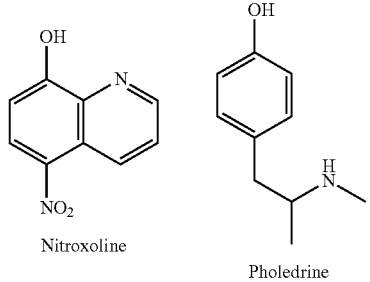

Nitroxoline

Pholedrine

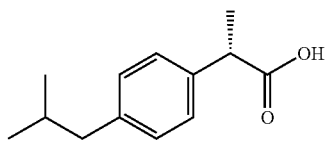

Diflunisal

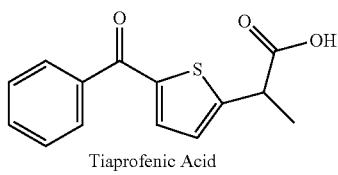

Ibuprofen

Oxyquinoline

Paracetamol

Tiaprofenic Acid

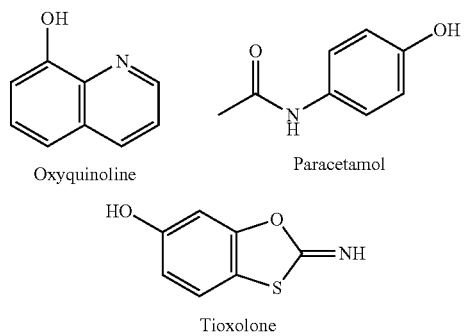

Tioxolone

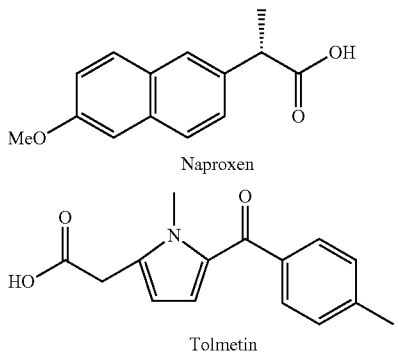

Naproxen

Tolmetin

Examples of biologically active compounds bearing carboxylic acid functional groups include but are not limited to Acemetacin, Aceclofenac, Acediasulfone, Adipiodone, Alminoprofen, Amlexanox, Anileridine, Baccofen, Balsalazide sodium, Bentiromide, Benzocaine, Bumetanide, Carprofen, Carzenide, Cinmetacin, Clometacin, Cromoglicic acid, Diclofenac, Diflunisal, Eprosartan, Fendosal, Flufenamic acid, Furosemide, Indometacin, Iobenzamic acid, Iocarmic acid, Iocetamic acid, Iodoxamic acid, Ioglycamic acid, Iophenoic acid, Iotroxic acid, Mefenamic acid, Naproxen, Nedocromil, Repaglinide, Salazosulfapyridine, Salicylic Acid, Salsalate, and Sarpogrelate.

Some structures of biologically active compounds bearing carboxyl functional groups that may be useful in present invention are shown below in FIG. 4.

FIG. 4.

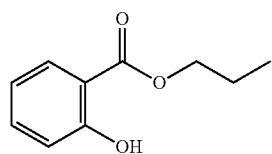

Methyl Salicylate

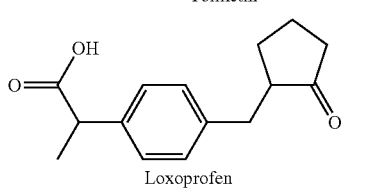

Loxoprofen

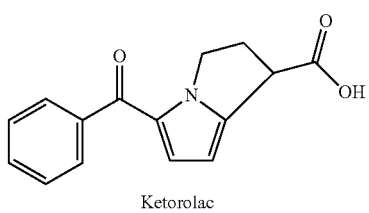

Ketorolac

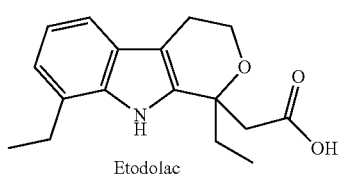

Etodolac

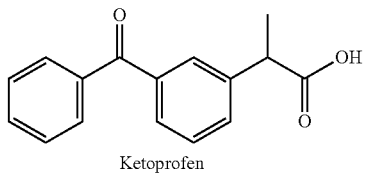

Ketoprofen

-continued

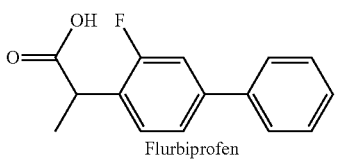
Flurbiprofen

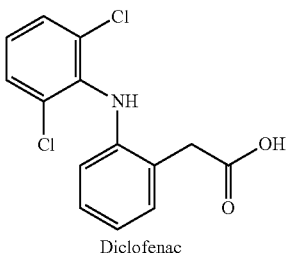
Diclofenac

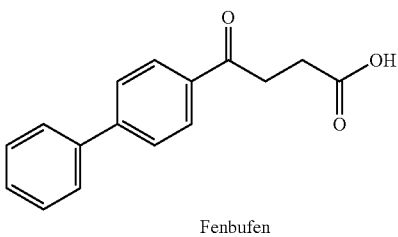
Fenbufen

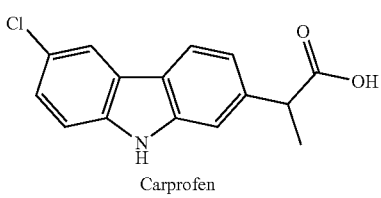
Carprofen

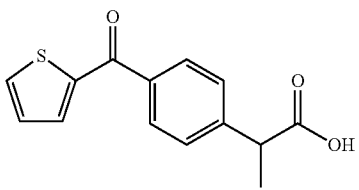
Suprofen

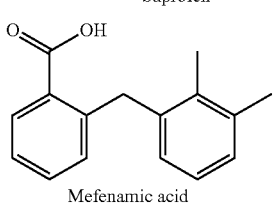
Mefenamic acid

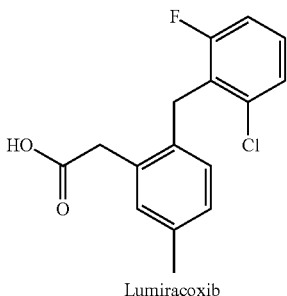
Lumiracoxib

-continued

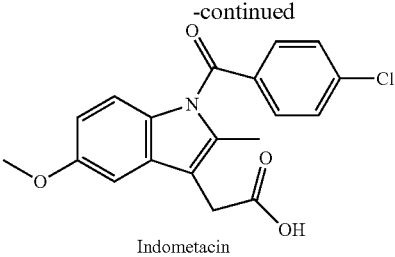
Indometacin

The rate of hydrolysis of functionalized triclosan monomers and oligomers will depend upon a number of factors, including the functionalization species used and the number of repeating units of functionalization species present on the functionalized triclosan monomers and oligomers (e.g., 1-6). Glycolic acid modified triclosan should hydrolyze faster than dioxanone modified one, where as lactic acid and caprolactone modified triclosan should take much longer to hydrolyze than glycolic acid and dioxanone modified triclosan. Furthermore, it is expected that the rate of hydrolysis will increase with the increase in the value of a and b. Thus, the desired time range may be obtained by altering the number of repeating units and type of functionalization species used to functionalize triclosan.

The present invention also provides blends or monomers and/or oligomers comprising one or more of the functionalization monomeric or oligomeric species with triclosan.

The present invention also provides polymer compositions comprising one or more of the functionalized monomers, oligomers, or di-, tri-, or polyamido compounds that are functionalized with triclosan.

In some other embodiments of the present invention, the inventive polymer compositions may be used as pharmaceutical carriers in a drug delivery matrix. The matrix is formed by mixing the polymer with a therapeutic agent. A vast variety of different therapeutic agents may be used in conjunction with the polymers of the invention. In general, therapeutic agents administered via the pharmaceutical compositions of the invention include, without limitation: antiinfectives such as antibiotics and antiviral agents; analgesics and analgesic combinations; anorexics; antihelmintics; antiarthritics; antiasthmatic agents; anticonvulsants; antidepressants; antidiuretic agents; antidiarrheals; antihistamines; antiinflammatory agents; antimigraine preparations; antinauseants; antineo-plastics; antiparkinsonism drugs; antipruritics; antipsychotics; antipyretics, antispasmodics; anticholinergics; sympathomimetics; xanthine derivatives; cardiovascular preparations including calcium channel blockers and beta-blockers such as pindolol and antiarrhythmics; antihypertensives; diuretics; vasodilators including general coronary, peripheral and cerebral; central nervous system stimulants; cough and cold preparations, including decongestants; hormones such as estradiol and other steroids, including corticosteroids; hypnotics; immunosuppressives; muscle relaxants; para-sympatyholytics; psychostimulants; sedatives; and tranquilizers; and naturally derived or genetically engineered proteins, polysaccharides, glycoproteins or lipoproteins.

The drug delivery matrix may be administered in any suitable dosage form such as oral, parenteral, subcutaneously as an implant, vaginally or as a suppository. Matrix formulations containing polymers of the invention may be formulated by mixing one or more therapeutic agents with the polymer. The therapeutic agent may be present as a liquid, a finely divided solid, or any other appropriate physical form. Typically, the matrix will include one or more additives, e.g., nontoxic auxiliary substances such as diluents, carriers, excipients, stabilizers or the like. However, the presence of such additives is entirely optional. Other suitable additives may be formulated with the polymers of this invention and pharmaceutically active agent or compound, however, if water is to be used it should be added immediately before administration.

Compositions comprising monomers and oligomers of the present invention, for example, those in a drug delivery matrix, may be suitable for administration via a route selected from oral, enteral, parenteral, topical, transdermal, ocular, vitreal, rectal, nasal, pulmonary, and vaginal.

Functionalized triclosan monomers and oligomers of the present invention, for example, those in a drug delivery matrix, have more controllable hydrolysis profiles, improved bioavailability, improved efficacy, and enhanced functionality. They may be used for applications, including biomedical applications, foodstuffs, cosmetics, medicaments, coatings and other uses readily apparent to one skilled in the art. Additional examples of drug delivery matrices, as well as the manner of providing and use of such matrices and may be found in Patent Publications US2006/0172983 and/or US2007/0251831, the disclosures of which are hereby incorporated herein by reference, in their entireties.

In other aspects of the present invention some functionalized triclosan monomers and oligomers of the present invention are further manufactured into formulations suitable for oral, rectal, parenteral (for example, subcutaneous, intramuscular, intradermal, or intravenous), transdermal, vitreal or topical administration. The most suitable route in any given case will depend on the nature and severity of the condition being treated and on the nature of the particular active compound that is being used. The formulations of a pharmaceutical composition are typically admixed with one or more pharmaceutically or veterinary acceptable carriers and/or excipients as are well known in the art.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion.

Formulations containing functionalized triclosan monomers and oligomers of the present invention suitable for parenteral administration conveniently comprise sterile aqueous preparations of the active compounds, where preparations are preferably isotonic with the blood of the intended recipient.

Formulations containing functionalized triclosan monomers and oligomers of the present invention suitable for rectal administration are preferably presented as unit dose suppositories.

Formulations containing functionalized triclosan monomers and oligomers of the present invention suitable for ocular or vitreal administration may be presented as bioabsorbable coatings for implantable medical devices, injectables, liquids, gels or suspensions.

Formulations or compositions containing functionalized triclosan monomers and oligomers of the present invention suitable for topical administration to the skin preferably take the form of an ointment, cream, lotion, paste, gel, spray, aerosol, or oil. Examples of carriers that conventionally used include Vaseline, lanoline, polyethylene glycols, alcohols, and combination of two or more thereof.

Formulations containing functionalized triclosan monomers and oligomers of the present invention suitable for transdermal administration may be presented as discrete patches adapted to remain in intimate contact with the epidermis of the recipient for a prolonged period of time.

The functionalized triclosan monomers and oligomers of the present invention are suitable for a wide range of devices and coatings, especially those where the antibacterial properties of triclosan are of benefit, including but not limited to medical devices and medical device coatings, surgical suture coatings, staple coatings, orthopedic device coatings, fabric coatings, surgical mesh coatings, clip coatings, stent coatings, needle coatings, catheters, and catheter coatings. Some other examples of coatings and/or devices within the ambit of the invention are described in Patent Publication US2006/0188547, the disclosure of which is hereby incorporated herein by reference, in its entirety.

In certain other embodiments, the polymer compositions of the present invention are used to coat a surface of a surgical article to enhance lubricity of the coated surface. The compositions may be applied as a coating using conventional techniques. For example, the polymer compositions may be solubilized in dilute solution of volatile organic solvent, e.g. acetone, methanol, ethyl acetate or toluene, and the article or medical device immersed in the solution to coat its surface. Once the surface is coated, the surgical article or device is removed from the solution where it maybe dried at an elevated temperature until solvent and any residual reactants are removed.

Numerous surgical articles (including but not limited to endoscopic instruments) may be coated with the polymer compositions of this invention to improve the surface properties of the article or device. Preferably, the surgical articles include surgical sutures, stents and needles. More preferably, the surgical article is a suture, still more preferably a suture attached to a needle. In some preferred embodiments, the suture is a synthetic absorbable suture. These sutures are derived, for example, from homopolymers and copolymers of lactone monomers such as glycolide, lactide, .epsilon.-caprolactone, 1,4-dioxanone, and trimethylene carbonate. In some embodiments, the preferred suture is a braided multifilament suture composed of polyglycolide or poly(glycolide-co-lactide).

The amount of coating polymer to be applied on the surface of a braided suture maybe readily determined empirically, and will depend on the particular copolymer and suture chosen. Ideally, the amount of coating copolymer applied to the surface of the suture may range from about 0.5 to about 30 percent of the weight of the coated suture, more preferably from about 1.0 to about 20 weight percent, most preferably from 1 to about 5 percent by weight.

Sutures coated with the polymers of this invention are desirable in certain embodiments because they have a more slippery feel, thus making it easier, in some instances, for the surgeon to slide a knot down the suture to the site of surgical trauma. In addition, the suture is more pliable, and therefore is easier for the surgeon to manipulate during use.

In other embodiments of the present invention where the article is a metal stent, the amount of coating applied to the surface of the article is an amount which creates a layer with a thickness ranging preferably between about 2 to about 20 microns on the stent, more preferably about 4 to about 8 microns.

In other embodiments of the present invention where the article is a surgical needle, the amount of coating applied to the surface of the article is an amount which creates a layer with a thickness ranging preferably between about 2 to about 20 microns on the needle, more preferably about 4 to about 8 microns.

The compounds and/or compositions of the present invention may be prepared in a number of ways well known to those skilled in the art. The compounds maybe synthesized, for example, by the methods described below, or variations thereon as appreciated by the skilled artisan. All processes disclosed in association with the present invention are contemplated to be practiced on any scale, including milligram, gram, multigram, kilogram, multikilogram or commercial industrial scale.

Examples of functionalized triclosan monomers and oligomers of the present invention are provided for some embodiments of the current invention. It maybe extended to other species. This selection is not meant to limit the scope of the invention in any way. Other variations in the procedure may be readily apparent to those skilled in the art.

EXAMPLES

SCHEME I

Functionalization of triclosan

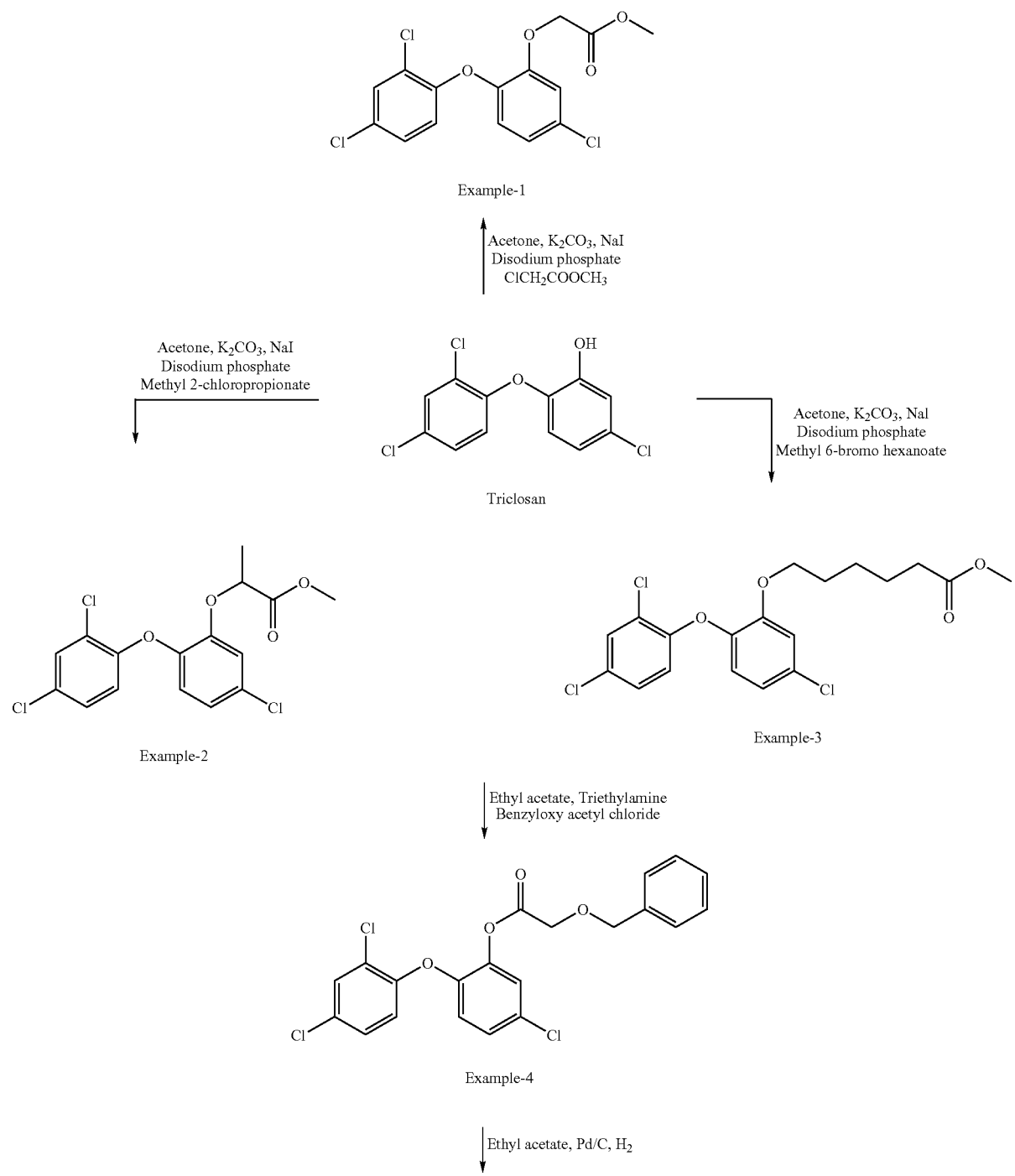

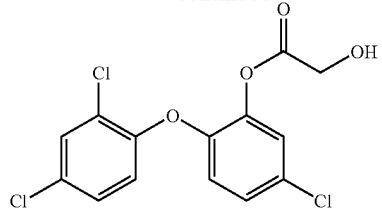

Example-5

Example 1

[5-Chloro-2-(2,4-dichloro-phenoxy)-phenoxy]-acetic acid methyl ester

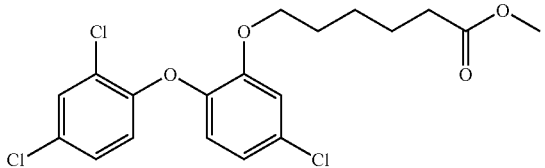

To a mixture of triclosan (50 grams, 173 mmol), anhydrous K$_2$CO$_3$ (100 grams, 723 mmol), sodium iodide (10 grams, 66.7 mmol) and disodium phosphate (10 grams, 70 mmol) in anhydrous acetone (500 mL) was added methyl chloro acetate (30 grams, 276 mmol). The reaction mixture was refluxed for 16 hours. Acetone was distilled and water (600 mL) was added. Crude 1 was extracted into ethyl acetate, dried over Na$_2$SO$_4$, distilled and purified by column chromatography on silica gel using hexane as eluant to give pure 1 (45 grams, 72.1%) as a white powder. m.p: 52-53° C. $^1$HNMR (CDCl$_3$) δ 3.78 (s, 3H, ester), 4.65 (s, 2H, OCH$_2$), 6.72 (d, 1H, Ar), 6.88 (m, 2H, Ar), 6.92 (m, 1H, Ar), 7.10 (m, 1H, Ar), 7.42 (s, 1H, Ar).

Example 2

2-[5-Chloro-2-(2,4-dichloro-phenoxy)-phenoxy]-propionic acid methyl ester

To a mixture of triclosan (50 grams, 173 mmol), anhydrous K$_2$CO$_3$ (100 grams, 723 mmol), sodium iodide (10 grams, 66.7 mmol) and disodium phosphate (10 grams, 70 mmol) in anhydrous acetone (500 mL) was added methyl 2-chloro propionate (32.25 grams, 263 mmol). The reaction mixture was refluxed for 24 hours. Acetone was distilled and water (600 mL) was added. Crude 2 was extracted into ethyl acetate, dried over Na$_2$SO$_4$, distilled and purified by column chromatography on silica gel using hexane as eluant to give pure 2 (35 grams, 54%) as a syrup. $^1$HNMR (CDCl$_3$) δ 1.48 (d, 3H, CH$_3$), 3.75 (s, 3H, ester), 4.72 (q, 1H, O—CH), 6.74 (d, 1H, Ar), 6.90 (m, 3H, Ar), 7.12 (dd, 1H, Ar), 7.42 (d, 1H, Ar).

Example 3

6-[5-Chloro-2-(2,4-dichloro-phenoxy)-phenoxy]-hexanoic acid methyl ester

To a mixture of triclosan (50 grams, 173 mmol), anhydrous K$_2$CO$_3$ (100 grams, 723 mmol), sodium iodide (10 grams, 66.7 mmol) and disodium phosphate (10 grams, 70 mmol), in anhydrous acetone (500 mL) was added methyl 6-bromo hexanoate (55 grams, 263 mmol). The reaction mixture was refluxed for 30 hours. Acetone was distilled and water (600 mL) was added. Crude 3 was extracted into ethyl acetate, dried over Na$_2$SO$_4$, distilled and purified by column chromatography on silica gel using hexane as eluant to give pure 3 (60 grams 90%) as a syrup. $^1$HNMR (CDCl$_3$) δ 1.24 (m, 2H, CH$_2$), 1.58 (m, 2H, CH$_2$), 1.64 (m, 2H, CH$_2$), 2.24 (t, 2H, CH$_2$), 3.65 (s, 3H, ester), 3.92 (t, 2H, OCH$_2$), 6.60 (d, 1H, Ar), 6.92 (m, 2H, Ar), 6.96 (d, 1H, Ar), 7.05 (d, 1H, Ar), 7.42 (s, 1H, Ar).

Example 4

Benzyloxy-acetic acid 5-chloro-2-(2,4-dichloro-phenoxy)-phenyl ester

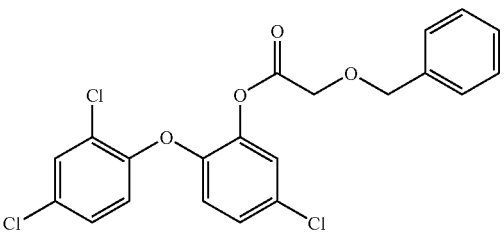

To a mixture of triclosan (7.53 grams, 26 mmol) and triethylamine (8.2 grams, 81 mmol) in acetone (50 mL) at 0° C. was added benzyloxy acetyl chloride (10 grams, 54.2 mmol) drop wise. The reaction mixture was stirred at room temperature for 18 hours. Solids were filtered off and poured onto cold water (100 mL). Crude 4 was extracted into chloroform, washed with 5% sodium bicarbonate solution (2×50 mL), and water (2×50 mL). The chloroform layer was dried over sodium sulphate and distilled off to get crude 4.

Example 5

Hydroxy-acetic acid 5-chloro-2-(2,4-dichloro-phenoxy)-phenyl ester

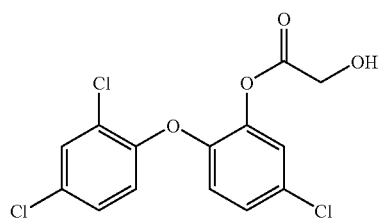

Benzyloxy-acetic acid 5-chloro-2-(2,4-dichloro-phenoxy)-phenyl ester 4 (5 grams) was dissolved in methanol (50 mL) in a pressure vessel, palladium on carbon (5%, 5 grams) was added and the mixture was stirred under an atmosphere of hydrogen (4 Kg) for 4 hours. The catalyst was removed by filtration and the methanol was distilled off to yield crude 5.

Example 6

[5-Chloro-2-(2,4-dichloro-phenoxy)-phenoxy]-acetic acid

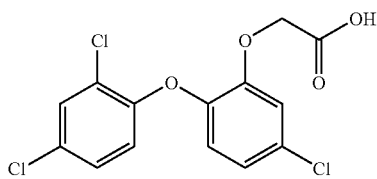

[5-Chloro-2-(2,4-dichloro-phenoxy)-phenoxy]-acetic acid methyl ester 1 (50 grams, 138.3 mmol) was added to 1.7 N—NaOH (150 mL) solution and heated to 90° C. for 2 hours on a water bath. The reaction mixture was cooled to 5° C., the pH of the reaction mixture was adjusted to 2 using a 3N-hydrochloric acid. The precipitate was filtered off to give crude 6, which was dried and recrystallised from a mixture of ethyl acetate:hexane (1:6) to get pure 6 (23 grams, 47.9%) as white powder. m.p: 127-129° C. $^1$H NMR (CDCl$_3$) δ 4.52 (s, 2H, CH$_2$), 6.36 (bs, 1H, COOH), 6.76 (d, 1H, Ar), 6.86 (m, 3H, Ar), 7.10 (cl, 1H, Ar), 7.40 (s, 1H, Ar).

SCHEME II

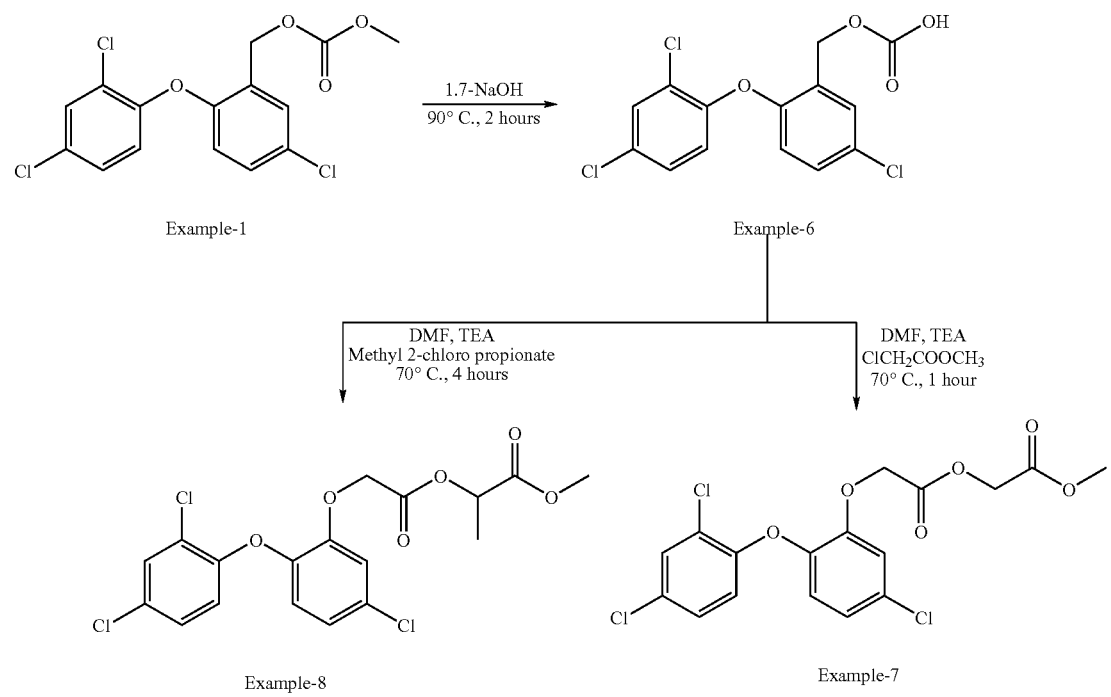

Example 7

[5-Chloro-2-(2,4-dichloro-phenoxy)-phenoxy]-acetic acid methoxy carbonyl methyl ester

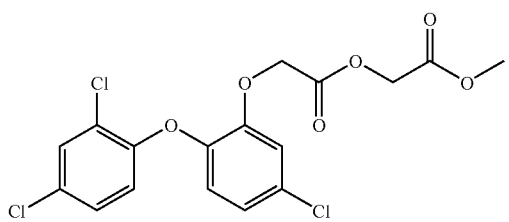

To a solution of [5-Chloro-2-(2,4-dichloro-phenoxy)-phenoxy]-acetic acid 6 (20 grams, 57.55 mmol) and triethylamine (9 grams, 88.94 mmol) in dimethylformamide (40 mL) was added methyl chloro acetate (8 grams, 73.71 mmol). The solution was heated at 70° C. for 1 hour. The solids were filtered off; the organic phase was poured onto ice (150 grams), extracted into ethyl acetate, washed with 5% sodium bicarbonate (2×50 mL) and water (2×50 mL). The ethyl acetate layer was then dried over sodium sulphate and ethyl acetate was distilled off to yield crude 7. The crude 7 was purified by recrystallisation using a mixture of ethyl acetate: hexane (1:6) to get pure 7 (17 grams, 70.4%) as off-white powder. m.p: 70-72° C. $^1$H NMR (CDCl$_3$) δ 3.80 (s, 3H, Ester), 4.68 (s, 2H, CH$_2$) 4.76 (s, 2H, CH$_2$), 6.72 (d, 1H, Ar), 6.92 (m, 3H, Ar), 7.12 (dd, 1H, Ar), 7.42 (d, 1H, Ar).

Example 8

2-{2-[5-Chloro-2-(2,4-dichloro-phenoxy)-phenoxy]-acetoxy}-propionic acid methyl ester

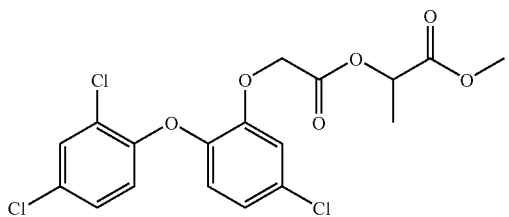

To a solution of [5-Chloro-2-(2,4-dichloro-phenoxy)-phenoxy]-acetic acid 6 (15 grams, 43.16 mmol) and triethyl amine (6.5 grams, 64.23 mmol) in dimethylformamide (30 mL) was added methyl 2-chloro propionate (5.8 grams, 47.32 mmol). The solution was heated at 70° C. for 4 hours. The solids were filtered off, the organic phase was poured onto ice (150 grams), extracted into ethyl acetate washed with 5% sodium bicarbonate (2×50 mL) and water (2×50 mL). The ethyl acetate layer was then dried over sodium sulphate and ethyl acetate was distilled off to yield crude 8. The crude 8 was purified by column chromatography over silica gel using a mixture of hexane:ethyl acetate (7:3) to get pure 8 (14 grams, 74.8%) as a light yellow syrup. $^1$H NMR (CDCl$_3$) δ 1.50 (d, 3H, CH$_3$), 3.75 (s, 3H, Ester), 4.75 (s, 2H, CH$_2$), 5.16 (q, 1H, CH), 6.75 (d, 1H, Ar), 6.95 (m, 3H, Ar), 7.10 (d, 1H, Ar), 7.40 (s, 1H, Ar).

SCHEME III

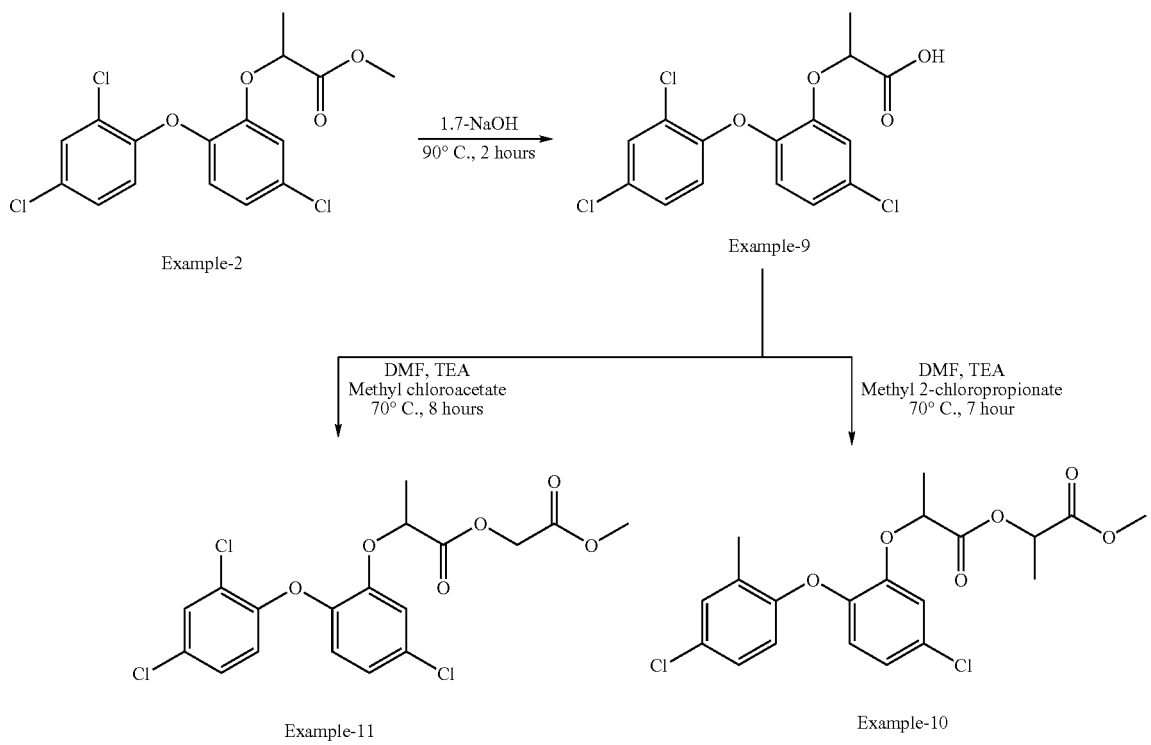

Example 9

2-[5-Chloro-2-(2,4-dichloro-phenoxy)-phenoxy]-propionic acid

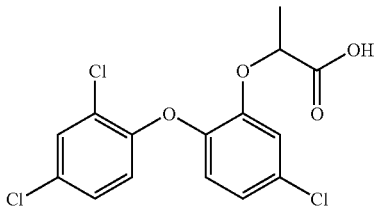

2-[5-Chloro-2-(2,4-dichloro-phenoxy)-phenoxy]-propionic acid methyl ester 2 (65 grams, 173.10 mmol) was added to 1.7N—NaOH (195 mL) solution. The solution was heated at 90° C. for 2 hours on a water bath. The reaction mixture was cooled to 5° C. and the pH of the reaction mixture was adjusted to 2 with 3N-hydrochloric acid and filtered to give crude 9, which was dried and recrystallised from a mixture of ethyl acetate:hexane (1:6) to get pure 9 (49 grams, 78.4%) as a white powder. m.p: 67-69° C. $^1$H NMR (CDCl$_3$) δ 1.60 (d, 3H, CH$_3$), 4.90 (q, 1H, CH), 6.80 (d, 1H, Ar), 6.90 (d, 1H, Ar), 7.00 (m, 2H, Ar), 7.18 (d, 1H, Ar), 7.50 (s, 1H, Ar), 8.56 (bs, 1H, COOH).

Example 10

2-[5-Chloro-2-(2,4-dichloro-phenoxy)-phenoxy]-propionic acid 1-methoxycarbonyl-ethyl ester

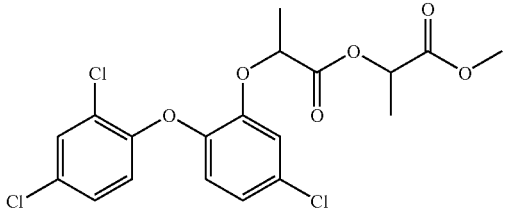

To a solution of 2-[5-Chloro-2-(2,4-dichloro-phenoxy)-phenoxy]-propionic acid (50 grams, 138.31 mmol) and triethyl amine (22.6 grams, 223.34 mmol) in dimethylformamide (100 mL) was added methyl 2-chloro propionate (21.3 grams, 174.23 mmol). The solution was heated at 70° C. for 7 hours. The solids were filtered off and the organic phase was poured on ice water (250 mL), extracted with ethyl acetate (3×100 mL) followed by washing with 5% sodium bicarbonate (2×50 mL) and water (2×50 mL). The ethyl acetate layer was then dried over sodium sulphate and ethyl acetate was distilled off to yield crude 10. The crude 10 was purified by column chromatography on silica gel using hexane:ethyl acetate (9:1) to get pure 10 (40 grams, 64.6%) as a light yellow syrup. $^1$H NMR (CDCl$_3$) δ 1.58 (m, 6H, CH$_3$), 3.72 (d, 3H, Ester), 4.80 (m, 1H, CH), 5.16 (m, 1H, CH), 6.80 (m, 1H, Ar), 6.98 (m, 3H, Ar), 7.10 (m, 1H, Ar), 7.42 (s, 1H, Ar).

Example 11

2-[5-Chloro-2-(2,4-dichloro-phenoxy)-phenoxy]-propionic acid methoxy carbonyl methyl ester

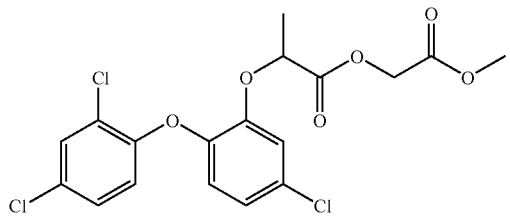

To a solution of 2-[5-Chloro-2-(2,4-dichloro-phenoxy)-phenoxy]-propionic acid (35 grams, 96.81 mmol) and triethyl amine (13 grams, 128.47 mmol) in dimethylformamide (70 mL) was added methyl chloroacetate (12.6 grams, 116.10 mmol). The solution was heated at 70° C. for 8 hours. The solids were filtered off; the organic phase was poured on ice water (200 mL), extracted with ethyl acetate (3×75 mL) followed by washing with 5% sodium bicarbonate (2×50 mL) and water (2×50 mL). The ethyl acetate layer was then dried over sodium sulphate and ethyl acetate was distilled off to yield crude 11. The crude 11 was purified by column chromatography on silica gel using chloroform as eluant to get pure 11 (20 grams, 47.6%) as a light yellow syrup. $^1$H NMR (CDCl$_3$) δ 1.55 (d, 3H, CH$_3$), 3.74 (s, 1H, Ester), 4.64 (s, 2H, CH$_2$), 4.82 (q, 1H, CH), 6.74 (d, 1H, Ar), 6.96 (m, 3H, Ar), 7.10 (dd, 1H, Ar), 7.42 (d, 1H, Ar).

SCHEME IV

Triclosan Dimer with Suberic Acid (control)

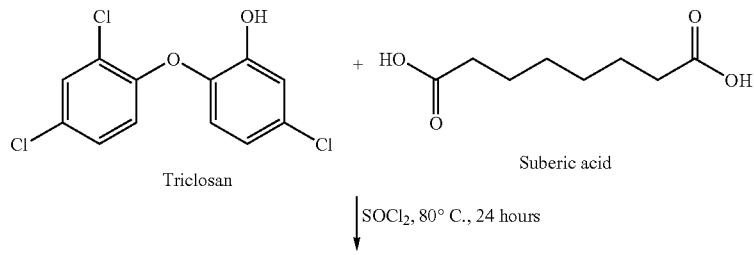

Triclosan      Suberic acid

SOCl$_2$, 80° C., 24 hours

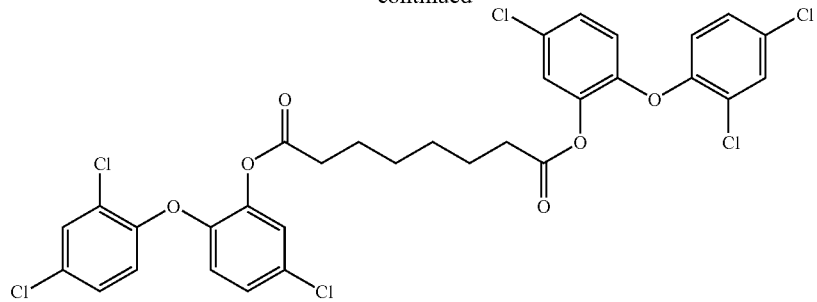

Example-12

Example 12

Control Sample

Octanedioic acid bis-[5-chloro-2-(2,4-dichloro-phenoxy)-phenyl]ester

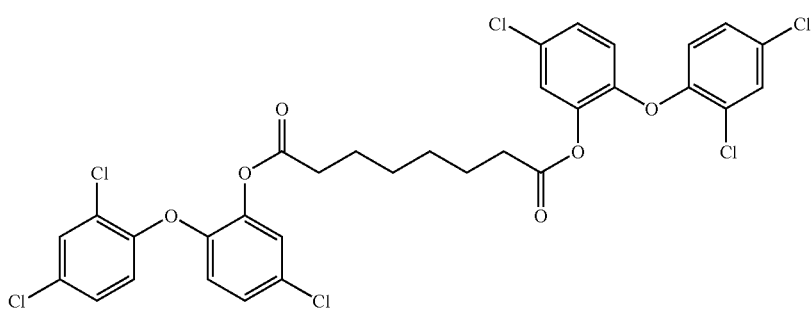

A solution of triclosan (17.4 grams, 60.09 mmol), suberic acid (5 grams, 28.70 mmol) and thionyl chloride (12.23 grams, 102.77 mmol) was refluxed at 80° C. for 24 hours. Excess thionyl chloride was distilled off and the product was taken in ethyl acetate followed by washing with 5% sodium bicarbonate solution. The ethyl acetate layer was then dried over sodium sulphate. The dried ethyl acetate layer was treated with charcoal. 80% of the ethyl acetate was distilled off and the rest of it was precipitated in hexane. The precipitate was filtered and dried to get 11 grams of 12 as a white powder with the m.p of 81-83° C. Analytical sample was prepared by recrystallisation from a mixture of ethyl acetate: hexane (1:6). m.p: 83-85° C. Mass: M+H$_2$O=735.5. $^1$H NMR (CDCl$_3$) δ 1.32 (t, 4H, CH$_2$), 1.61 (t, 4H, CH$_2$), 2.44 (t, 4H, CH$_2$), 6.84 (m, 4H, Ar), 7.16 (m, 6H, Ar), 7.43 (s, 2H, Ar).

| Hydrolysis | |
|---|---|
| Dimer | 500 mg |
| Aldrich pH9 buffer | 50 mL |
| Temperature | 100° C. |

This control sample did not hydrolyze even in 48 hours

SCHEME V

Triclosan Dimer with Hydroquinone PDO

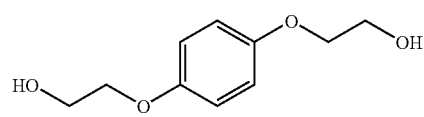

Hydroquinone bis ethanol

| DMF, NaH
ClCH$_2$COOH
↓

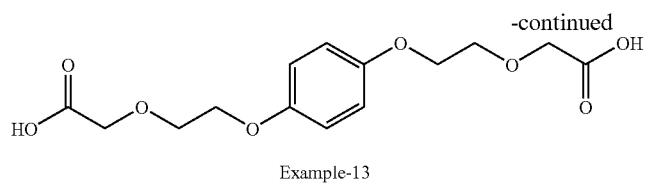
Example-13

↓ SOCl₂

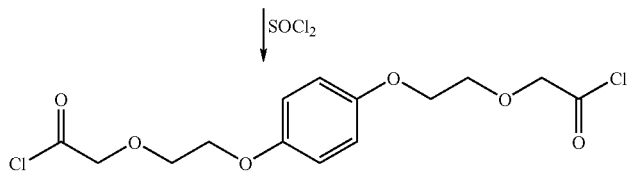
Example-14

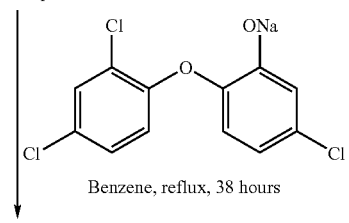
Benzene, reflux, 38 hours

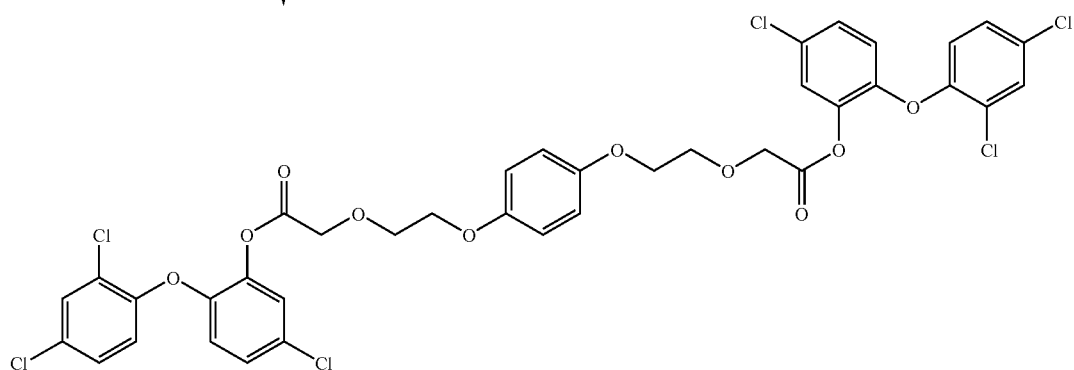
Example-15

Example 13

{2-[4-(2-Carboxymethoxy-ethoxy)-phenoxy]-ethoxy}-acetic acid

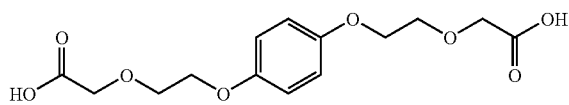

To a suspension of sodium hydride (60%, 132 grams, 3.30 moles) in anhydrous dimethylformamide (600 mL) under nitrogen atmosphere at 0° C. was added hydroquinone bis ethanol (150 grams, 756.7 mmoles) in small for hour, later stirred at room temperature for one hour. To the above mixture was added a solution of chloro acetic acid (195 grams, 2.06 moles) in anhydrous dimethylformamide (300 mL) very cautiously drop wise as the reaction is exothermic. Later the reaction is maintained at 80° C. for one hour and left at room temperature for 16 hours. Reaction mixture carefully poured onto ice (3 kg), extracted with ethyl acetate (2×500 mL) and organic phase discarded. The pH of the aqueous layer was adjusted to 2 with 3N-hydrochloric acid and extracted into ethyl acetate. The ethyl acetate extract was dried over sodium sulphate followed by distillation to yield crude 13 (120 grams, 50.5%) which was carried over to next stage. ¹H NMR (CDCl₃) δ 3.84 (m, 2H, CH₂), 4.06 (m, 4H, CH₂×2), 6.82 (s, 2H, Ar).

Example 14

{2-[4-(2-Chlorocarbonylmethoxy-ethoxy)-phenoxy]-ethoxy}-acetyl chloride

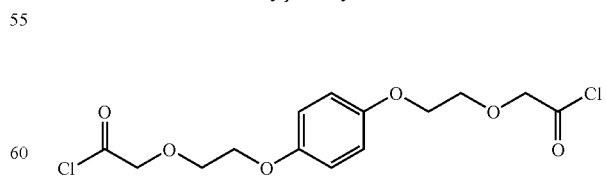

A mixture of {2-[4-(2-Carboxymethoxy-ethoxy)-phenoxy]-ethoxy}-acetic acid 13 (5 g) and thionyl chloride (12 mL) was refluxed for 6 hours, excess of thionyl chloride was distilled off to get crude 14, which was used as such for next reaction.

Example 15

[2-(4-{2-[5-Chloro-2-(2,4-dichloro-phenoxy)-phenoxycarbonylmethoxy]-ethoxy}phenoxy)-ethoxy]-acetic acid 5-chloro-2-(2,4-dichloro-phenoxy)-phenyl ester

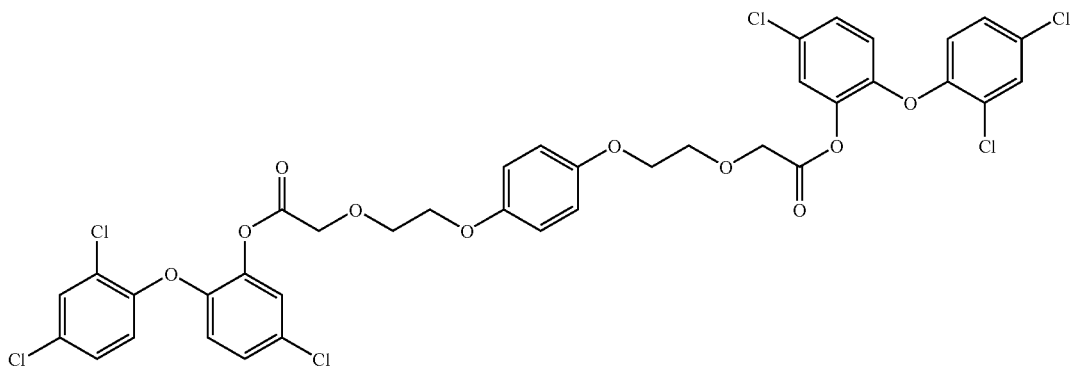

To a mixture of benzene (90 mL) and triclosan sodium (9 grams, 28.89 mmol) maintained at 10° C., was added dropwise a solution of acid chloride 14 in benzene. The reaction mixture was stirred at room temperature for 38 hours. The solids were filtered off and the benzene layer washed with 5% sodium sulphate followed by charcoal treatment. 90% of the benzene was distilled off and the remaining solution was precipitated into diisopropyl ether. The precipitate was filtered off, dried and recrystallised from ethyl acetate to get pure 15 (4.5 grams) as a white powder. m.p: 132-135° C. $^1$H NMR (CDCl$_3$) δ 3.78 (t, 4H, CH$_2$), 4.02 (t, 4H, CH$_2$), 4.40 (s, 4H, CH$_2$), 6.84 (s, 4H, Ar), 7.00 (d, 2H, Ar), 7.12 (d, 2H, Ar), 7.42 (m, 4H, Ar), 7.52 (d, 2H, Ar), 7.76 (d, 2H, Ar).

| Hydrolysis | |
|---|---|
| Dimer | 500 mg |
| Aldrich pH9 buffer | 50 mL |
| Temperature | 100° C. |

Hydrolyzed in 6 hour 30 minutes

Alternative Preparation of Compound 15

Triclosan Dimer with Hydroquinone PDO

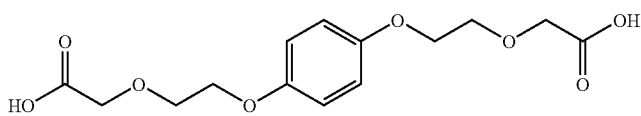

Example-13

SOCl$_2$

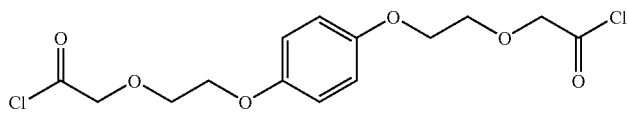

Example-14

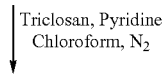

Triclosan, Pyridine
Chloroform, N$_2$

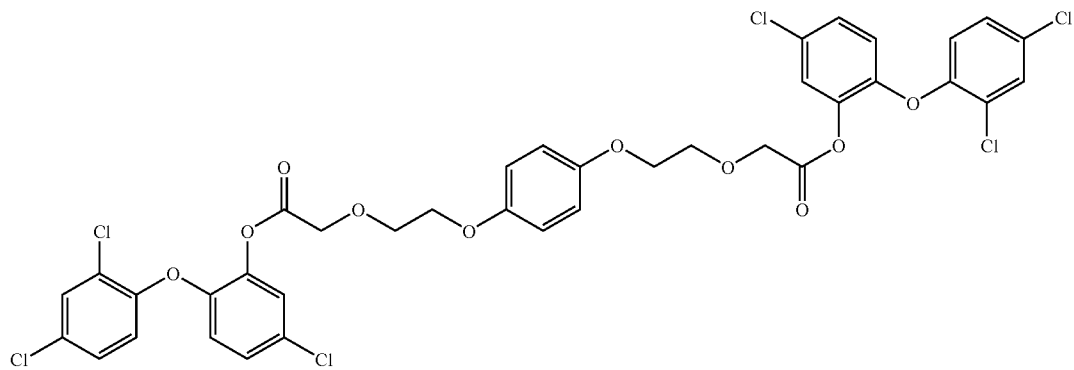

Example-15

PDO Acid Chloride

A mixture of acid 13 (10 grams, 62.40 mmol) and thionyl chloride (25 mL, 342.64 mmol) was stirred at room temperature for one hour and heated to reflux for 20 hours. Excess of thionyl chloride was distilled off and toluene (25 mL) was added, distilled off toluene and this process was repeated another time, to get the acid chloride 14 which was used as such for next stage.

Dimer

To a solution of triclosan (6.19 grams, 21.37 mmol) and pyridine (2.25 grams, 28.44 mmol) in chloroform (40 mL) at 0° C. under $N_2$ atmosphere was added a solution of acid chloride (5 grams, 14.24 mmol) in chloroform (10 mL) dropwise and stirred at the same temperature for one hour. TLC showed the presence of triclosan by around 5%, so we added further quantity of acid chloride (1 gram, 2.84 mmol) and stirred further for 3 hours. TLC showed the presence of triclosan by around 5%.

The reaction mixture was washed with water (2×100 mL) and 5% Sodium carbonate (3×100 mL). It was dried over sodium sulphate, treated with Charcoal and distilled to get crude compound, which was slurried in diisopropyl ether (25 mL), filtered, dried and recrystallised from ethyl acetate to get pure dimmer 15 (2.5 grams) as a white powder. m.p: 127.6-129.6° C.

| Hydrolysis Data | |
| --- | --- |
| Dimer | 0.5 grams |
| pH 9 buffer | 50 mL |
| Temperature | 100° C. |

Hydrolyzed in 28 hours 30 minutes

| | |
| --- | --- |
| Dimer | 0.5 grams |
| pH 9 buffer | 50 mL |
| Temperature | 50° C. |

Hydrolyzed in 150 hours

SCHEME-VI

Triclosan Dimer with Hydroquinone Diglycolic acid

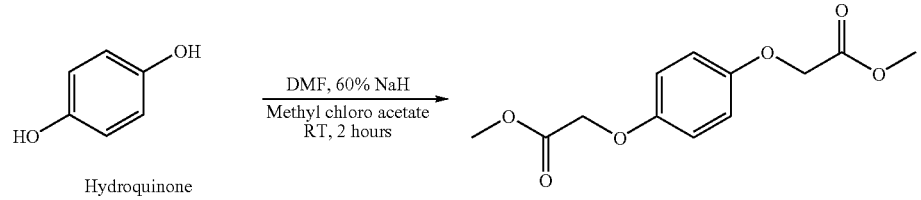

Example-16

NaOH, Water
70° C., 20 hours

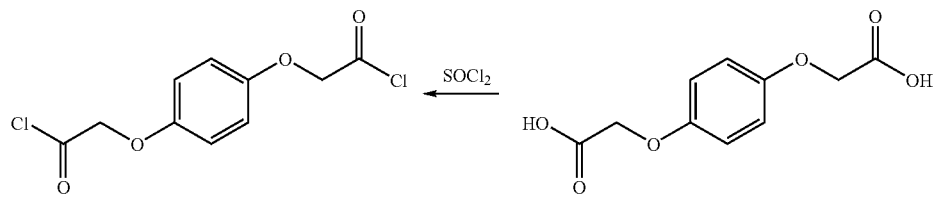

Example-18   Example-17

Triclosan Sodium
Benzene

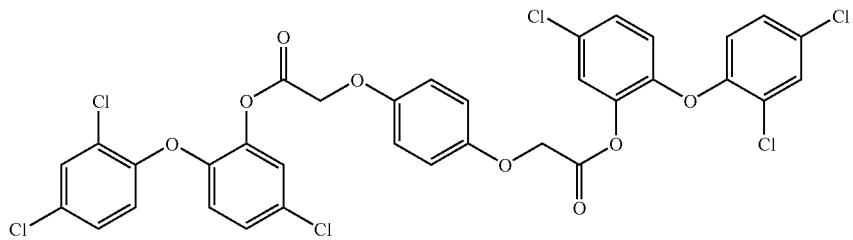

Example-19

Example 16

(4-Methoxycarbonylmethoxy-phenoxy)-acetic acid methyl ester

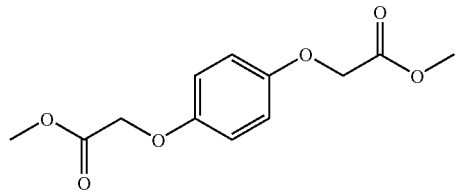

To a mixture of sodium hydride (60%, 92 grams, 2.3 moles) in DMF (400 mL) at 0° C. was added hydroquinone (100 grams, 909 mmol) carefully and stirred for 30 minutes. Methyl chloro acetate (247 grams, 2.276 moles) was added drop wise and later stirred at room temperature for 2 hours. Reaction mixture was carefully quenched into ice water (2 lit). Crude 16 was filtered, dried and recrystallised from a mixture of ethyl acetate:hexane (1:6) to give pure 16 (95 grams, 41.1%) as a white powder. M.p: 96-98° C. $^1$H NMR (CDCl$_3$) δ 3.68 (s, 3H, Ester), 4.54 (s, 2H, OCH$_2$), 6.82 (s, 2H, Ar).

Example 17

(4-Carboxymethoxy-phenoxy)-acetic acid

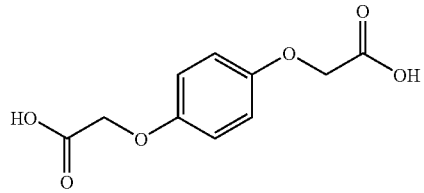

(4-Methoxycarbonylmethoxy-phenoxy)-acetic acid methyl ester 16 (100 grams, 394 mmol) was added to 3.25 M-sodium hydroxide solution (600 mL) and heated to 70° C. for 20 hours and poured onto 1 liter of ice cold water. The pH of the solution was adjusted to 1 with concentrated hydrochloric acid. Crude 17 was filtered, dried and recrystallised from DMF by precipitating with water to give pure 17 (60 grams, 67.4%) as a white powder. M.p: 254-256.5° C. $^1$H NMR (CDCl$_3$+DMSO, d$_6$) δ 4.44 (s, 2H, OCH$_2$), 6.72 (s, 2H, Ar).

Example 18

(4-Chlorocarbonylmethoxy-phenoxy)-acetyl chloride

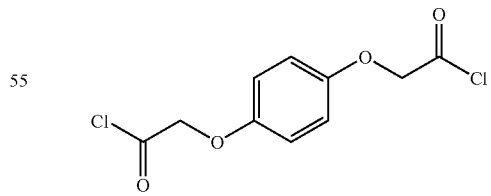

10 grams of (4-Carboxymethoxy-phenoxy)-acetic acid 17 was taken in to thionyl chloride (30 mL) and refluxed for 6 hours, excess of thionyl chloride was distilled off to get crude 18, which was used as such for next reaction.

Example 19

{4-[5-Chloro-2-(2,4-dichloro-phenoxy)-phenoxycarbonylmethoxy]-phenoxy}-acetic acid 5-chloro-2-(2,4-dichloro-phenoxy)-phenyl ester

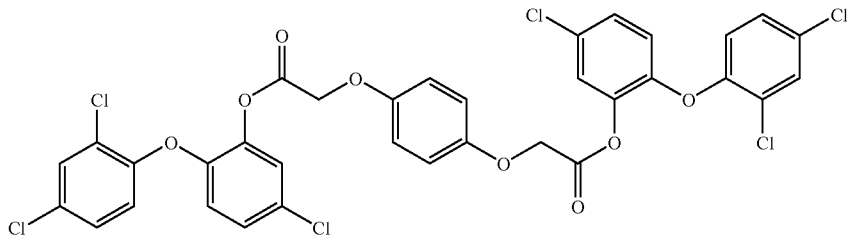

To a mixture of triclosan sodium in 100 ml of benzene maintained at 10° C. was added a solution of (4-Chlorocarbonylmethoxy-phenoxy)-acetyl chloride 18 (5 grams) in benzene drop wise and stirred at room temperature over night. The TLC showed the presence of unreacted triclosan. Further 5 grams of (4-Chlorocarbonylmethoxy-phenoxy)-acetyl chloride 18 was added and refluxed over night. The TLC showed with presence of triclosan. Thionyl chloride (30 mL) was added and refluxed for 72 hours. The TLC showed the completion of reaction. Excess thionyl chloride along with benzene was distilled off under vacuum, the product was taken in to 50 mL ethyl acetate, washed with 5% sodium bicarbonate solution, dried over sodium sulphate and distilled wise thionyl chloride (30 mL) and further refluxed for 24 hours. The TLC showed the presence of unreacted triclosan. To this refluxing solution was added dimethylformamide (0.5 mL) and continued reflux for additional 24 hours. The TLC showed the completion of reaction, excess thionyl chloride and toluene were distilled off. The compound was dissolved in ethyl acetate (100 mL), washed with 5% Sodium bicarbonate solution, dried over sodium sulphate and distilled to get crude 19, which was purified by column chromatography on silica gel using hexane:benzene (8:2) as eluant to get pure 19 (12 grams) as light yellow syrup.

$^1$H NMR (CDCl$_3$) 4.76 (s, 2H, CH$_2$), 6.79 (m, 2H, Ar), 6.86 (d, 2H, Ar), 7.22 (m, 3H, Ar), 7.45 (d, 1H, Ar).

Another Method of Preparation of Compound 19

Triclosan Dimer with Hydroquinone Diglycolic acid

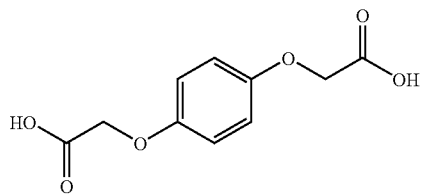 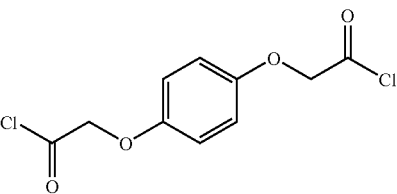

Example-17     Example-18

Triclosan Pyridine
Chloroform, N$_2$

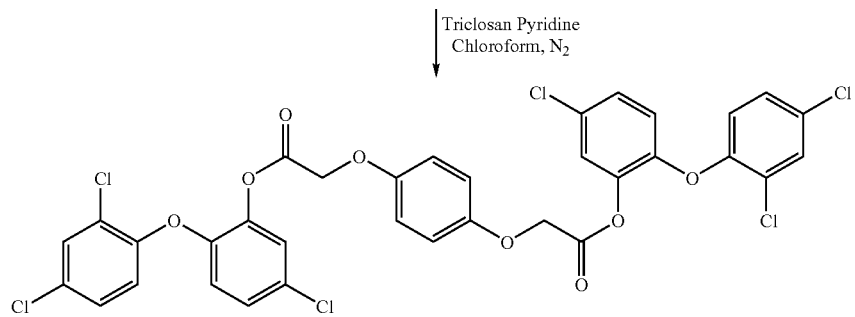

Example-19 to get crude which was purified by column chromatography using hexane:benzene (8:2) to get pure 19 (1 gram) as a light yellow syrup.

Alternative Method of Preparation of Compound 19

To a refluxing solution of triclosan (54 grams, 186.49 mmol) and (4-Carboxymethoxy-phenoxy)-acetic acid 17 (25 grams, 110.61 mmol) in toluene (150 mL) was added a drop Acid Chloride A mixture of diacid 17 (15 grams, 66.31 mmol), Thionyl chloride (75 mL, 1.027 mol) and dimethylformamide (0.5 mL) was stirred at room temperature for 1 hour and later heated to reflux for 20 hours. Excess of thionyl chloride was distilled off, toluene (25 mL was added, distilled off Toluene and this process was repeated another time, to get the acid chloride 18 which was used as such for next stage.

Dimer

To a solution of triclosan (8.25 grams, 28.49 mmol) and pyridine (3 grams, 37.92 mmol) in chloroform (40 mL) at 0° C. under $N_2$ atmosphere was added dropwise a solution of acid chloride 18 (5 grams, 19 mmol) in chloroform (10 mL) and stirred at the same temperature for 2 hours 45 minutes. Reaction mass was diluted with chloroform (200 mL), washed with water (4×100 mL), dried over sodium sulphate, given charcoal treatment and distilled to get crude product 19 as syrup, which crystallized to solid product in 12 hours. The product was washed with hexane (100 mL) followed by diisopropyl ether (25 mL) to get dimer 19 (7 grams) as off white powder. m.p: 124-131° C. A sample on recrystallization gave a melting point of 130-132° C. as a white powder Hydrolysis Data for Compound 19 Under Different Conditions

| Compound 19 | 0.5 grams |
| pH 9 buffer | 50 mL |
| Temperature | 100° C. |

Hydrolyzed in 23 hours 30 minutes

| Compound 19 | 0.5 grams |
| pH 9 buffer | 50 mL |
| Temperature | 50° C. |

Hydrolyzed in 150 hours

| Compound 19 | 0.5 grams |
| pH 7 buffer | 50 mL |
| Temperature | 50° C. |

By TLC it hydrolyzed around 5% in 48 hours

| Compound 19 | 0.5 grams |
| pH 7 buffer | 50 mL |
| Temperature | 100° C. |

By TLC it hydrolyzed around 15% in 48 hours

SCHEME VII

Triclosan Dimer with Diglycolic acid

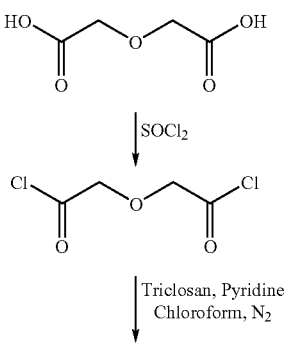

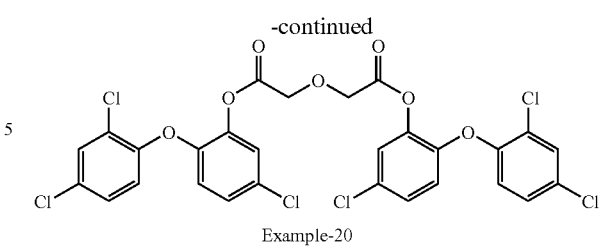

Example-20

Diglycolyl Chloride

A solution of diglycolic acid (25 grams, 186.44 mmol) and Thionyl chloride (30 mL, 411.17) was refluxed for 5 hours. Excess thionyl chloride was distilled off and the acid chloride was purified by high vacuum distillation to get pure product (25 grams, 78.6%) as a light yellow liquid. bp: 84-87° C./2 mm Hg.

Dimer (Batch-01)

To a solution of triclosan (23 grams, 79.43 mmol) and pyridine (10.9 mL, 134.91 mmol) in chloroform (110 mL) at 0° C. under $N_2$ atmosphere, was added a solution of diglycolyl chloride (11 grams, 64.33 mmol) in chloroform (15 mL) dropwise over a period of 30 minutes and stirred at the same temperature for 2 hours. It was then placed in a refrigerator over night. The reaction mixture was washed with water (2×100 mL), 5% Sodium bicarbonate (3×100 mL), 5% copper sulphate solution (3×100 mL) and water (2×100 mL). It was dried over sodium sulphate and the chloroform was distilled off under vacuum to get the dimer 20 (15 grams), as a yellow thick syrup. $^1H$ NMR (CDCl$_3$) δ 4.44 (s, 2H, CH$_2$), 6.80 (d, 1H, Ar), 6.89 (d, 2H, Ar), 7.20 (m, 3H, Ar), 7.43 (d, 1H, Ar).

Dimer (Batch-02)

To a solution of triclosan (16.7 grams, 57.67 mmol) and pyridine (9 mL, 111.39 mmol) in chloroform (100 mL) at 0° C. under $N_2$ atmosphere, was added a solution of diglycolyl chloride (9 grams, 52.63 mmol) in chloroform (10 mL) drop wise over a period of 30 minutes and stirred at the same temperature for 2 hours. The reaction mixture was washed with water (2×100 mL), 5% Sodium bicarbonate (3×100 mL), 5% copper sulphate solution (3×100 mL), water (2×100 mL). It was dried over sodium sulphate and the chloroform was distilled off under vacuum to get the dimer (15 grams), as a yellow thick syrup, which on standing for two days solidified. This solid was slurried in hexane (50 mL) to get the crude dimer 20 (9 grams) as brown powder.

Purification: 14 grams of crude dimer dissolved in chloroform (100 mL) washed with 5% sodium bicarbonate solution (3×100 mL), water (2×100 mL), dried over sodium sulphate, treated with activated carbon, distilled off 90% chloroform and precipitated with diisopropyl ether, cooled to 10° C., filtered and dried to get the pure dimmer 20 (7.6 grams) as white powder. Mp: 84.8-86.5° C. $^1H$ NMR (CDCl$_3$) δ 4.44 (s, 2H, CH$_2$), 6.80 (d, 1H, Ar), 6.89 (d, 2H, Ar), 7.20 (m, 3H, Ar), 7.43 (d, 1H, Ar).

| Hydrolysis | |
| --- | --- |
| Dimer | 0.5 grams |
| pH 9 buffer | 50 mL |
| Temperature | 100° C. |

Hydrolyzed in 25 hours
| | |
|---|---|
| Dimer | 0.5 grams |
| pH 9 buffer | 50 mL |
| Temperature | 50° C. |
Hydrolyzed in 102 hours
| | |
|---|---|
| Dimer | 0.5 grams |
| pH 7 buffer | 50 mL |
| Temperature | 100° C. |
Hydrolyzed 50% only in 53 hours
Triclosan Dimer with Dicaproic Acid Diglycolate
Example 21
Synthesis of Compound 21
(a) Synthesis of Benzyl-6-bromohexanoate
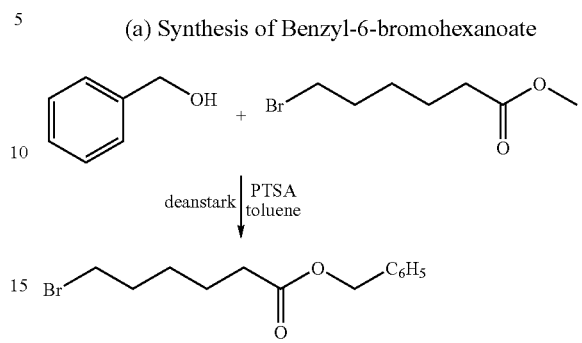
Scheme VIII
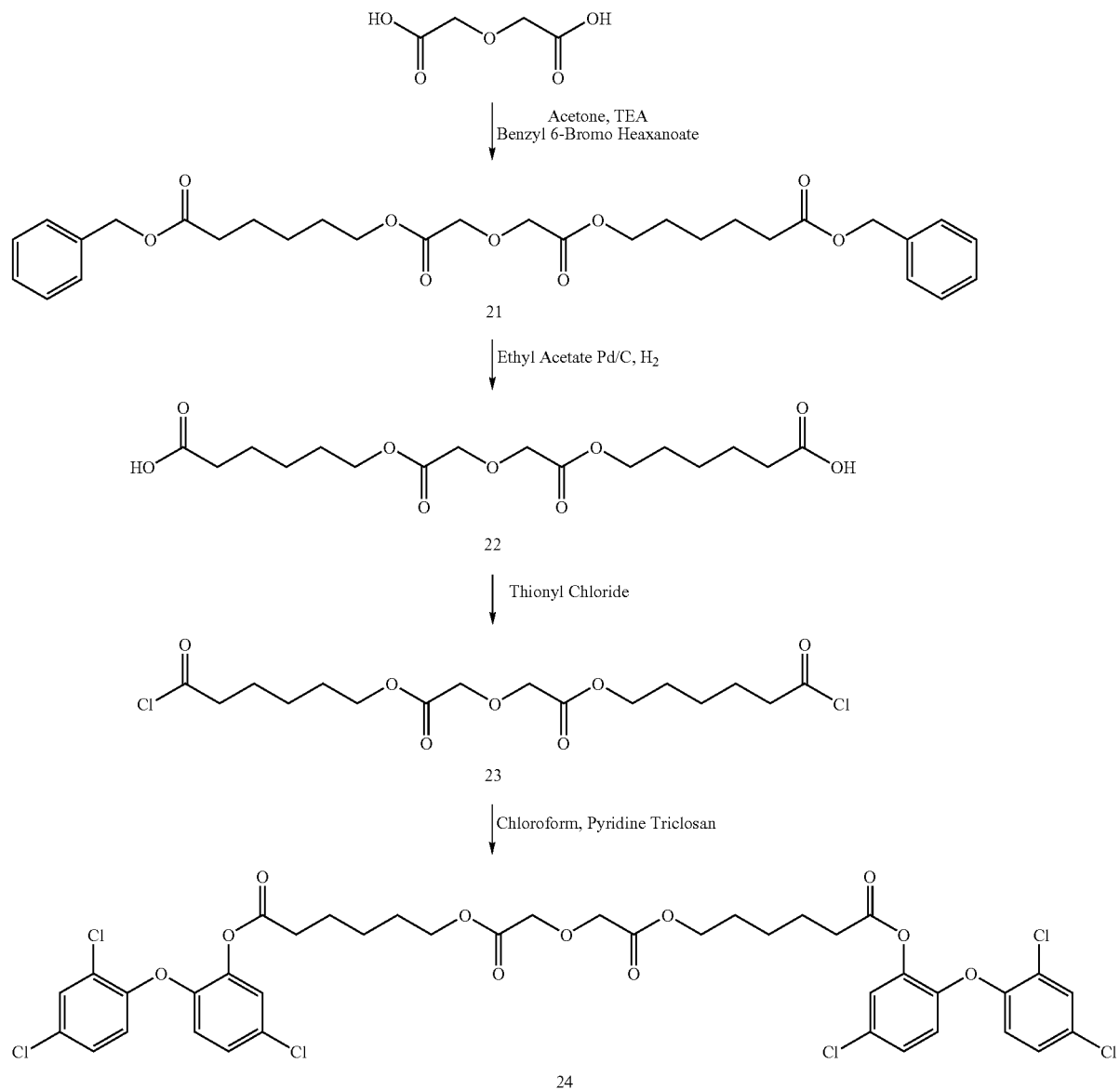

Into a clean and dry 3 liter, 3 necked round bottom flask equipped with a desiccant tube was added 250 grams of benzyl alcohol, 496 grams of 6-bromohexanoic acid, 1500 ml of toluene and 10 grams of p-toluene sulphonic acid. The flask was left with stirring in an oil bath maintained at 140° C. for one hour when all the starting material disappeared as determined by thin layer chromatography. The reaction mixture was cooled to room temperature and washed with 5% solution of sodium bicarbonate followed by water. The toluene layer was dried using sodium sulphate and the toluene was distilled off using high vacuum distillation to yield 540 grams of colorless benzyl-6-bromohexanoate with a boiling point of 160° C. and a purity of 99% as determined by gas chromatography.

(b) Addition of benzyl-6-bromohexanoate on diglycolic acid

Into a clean and dry 2 liter, 3 necked round bottom flask equipped with a desiccant tube was added 100 grams of diglycolic acid in 1 liter of acetone. 310 ml of anhydrous trimethylamine was added to this solution and stirred at room temperature for about 10 minutes. To this stirring solution was added dropwise 436 grams of benzyl-6-bromohexanoate. The flask was left with stirring at room temperature for 24 hours following which the reaction mixture was precipitated in cold water followed by extraction using ethyl acetate. The ethyl acetate layer was washed with 5% solution of sodium bicarbonate followed by drying using sodium sulphate. Ethyl acetate was distilled off using high vacuum distillation to yield 257 grams of colorless liquid 21.

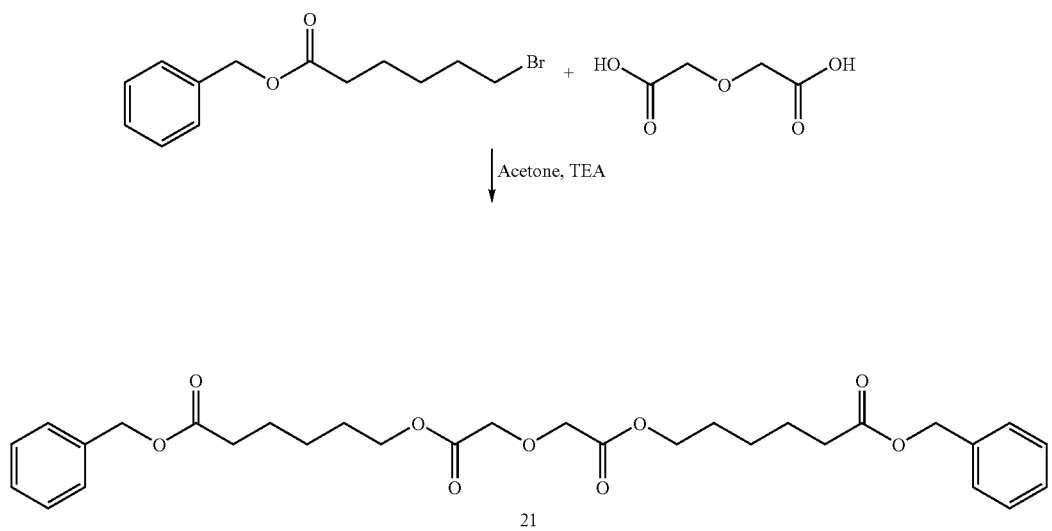

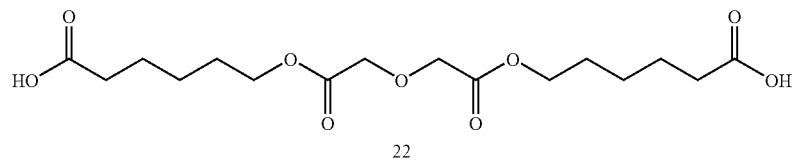

Example 22

Synthesis of Diglycolic Acid Dicaproic Acid

Into a hydrogenation apparatus was added 250 grams of 21 dissolved in 500 ml of Ethyl acetate. 2 grams of 10% Palladium on Carbon was added to the solution and the resulting reaction mixture in the pressure vessel was purged with hydrogen maintained at a pressure of 4 kg and stirred for 16 hours. The completion of reaction was determined by disappearance of starting material using thin layer chromatography. The reaction mixture after completion was filtered using the high flow bed and washed with ethyl acetate. Ethyl acetate was distilled off to yield 250 grams of crude 22. The resulting crude product was purified via crystallization using a mixture of ethyl acetate and hexane to yield 185 grams of pure 22 with a melting point of 74-76° C.

Example 23

Synthesis of Diglycolic Acid Dicaproic Acid Chloride

A clean and dry 250 ml round bottom flask equipped with a nitrogen inlet was charged with 50 grams of diglycolic acid dicaproic acid 22 and 70 ml of thionyl chloride. The flask was left for stirring at 80° C. for 24 hours following which thionyl chloride was distilled under vacuum. 60 ml of toluene was added to the reaction mixture and any remaining thionyl chloride was distilled off the reaction mixture along with toluene under high vacuum to yield 45 grams of light yellow colored acid chloride 23.

Example 24

Synthesis of Dimer of Triclosan From Diglycolic Acid Dicaproic Acid Chloride

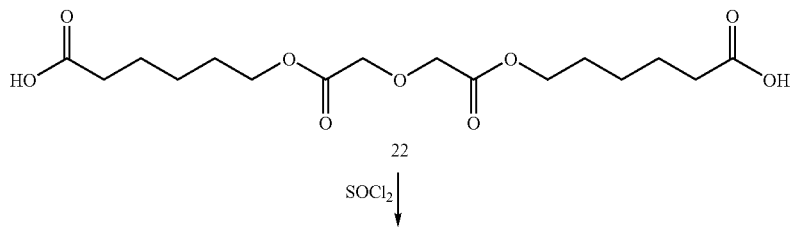

22

SOCl₂ ↓

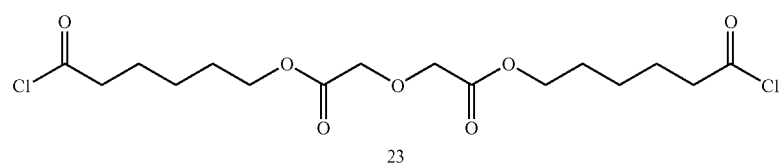

23

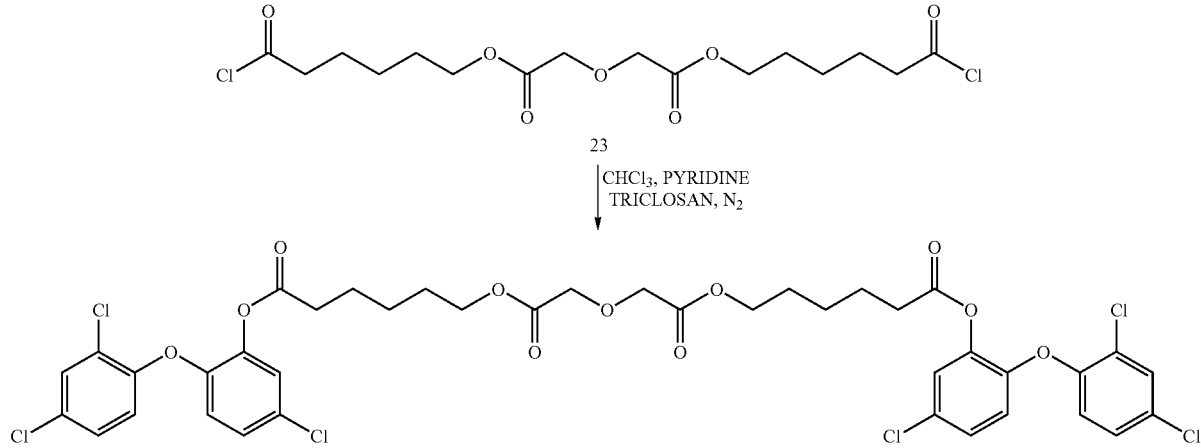

Into a clean and dry 1 liter, 3 necked round bottom flask equipped with a nitrogen inlet was added 37.7 grams of triclosan in 200 ml of chloroform. 16 ml of pyridine was added to the reaction mixture and the reaction mixture was cooled to 0° C. along with stirring. To this stirring solution was added dropwise 45 grams of diglycolic acid dicaproic acid chloride 23 dissolved in 50 ml of chloroform and the reaction was left for stirring at 0° C. for two hours following which the reaction mixture was precipitated in cold water followed by extraction using ethyl acetate. The ethyl acetate layer was washed with 5% solution of sodium bicarbonate followed by 1% solution of copper sulphate and the ethyl acetate fraction was dried using sodium sulphate. Ethyl acetate was distilled off using high vacuum distillation and the crude compound was purified using column chromatography to yield 35 grams of light yellow colored syrup of dimer 24.

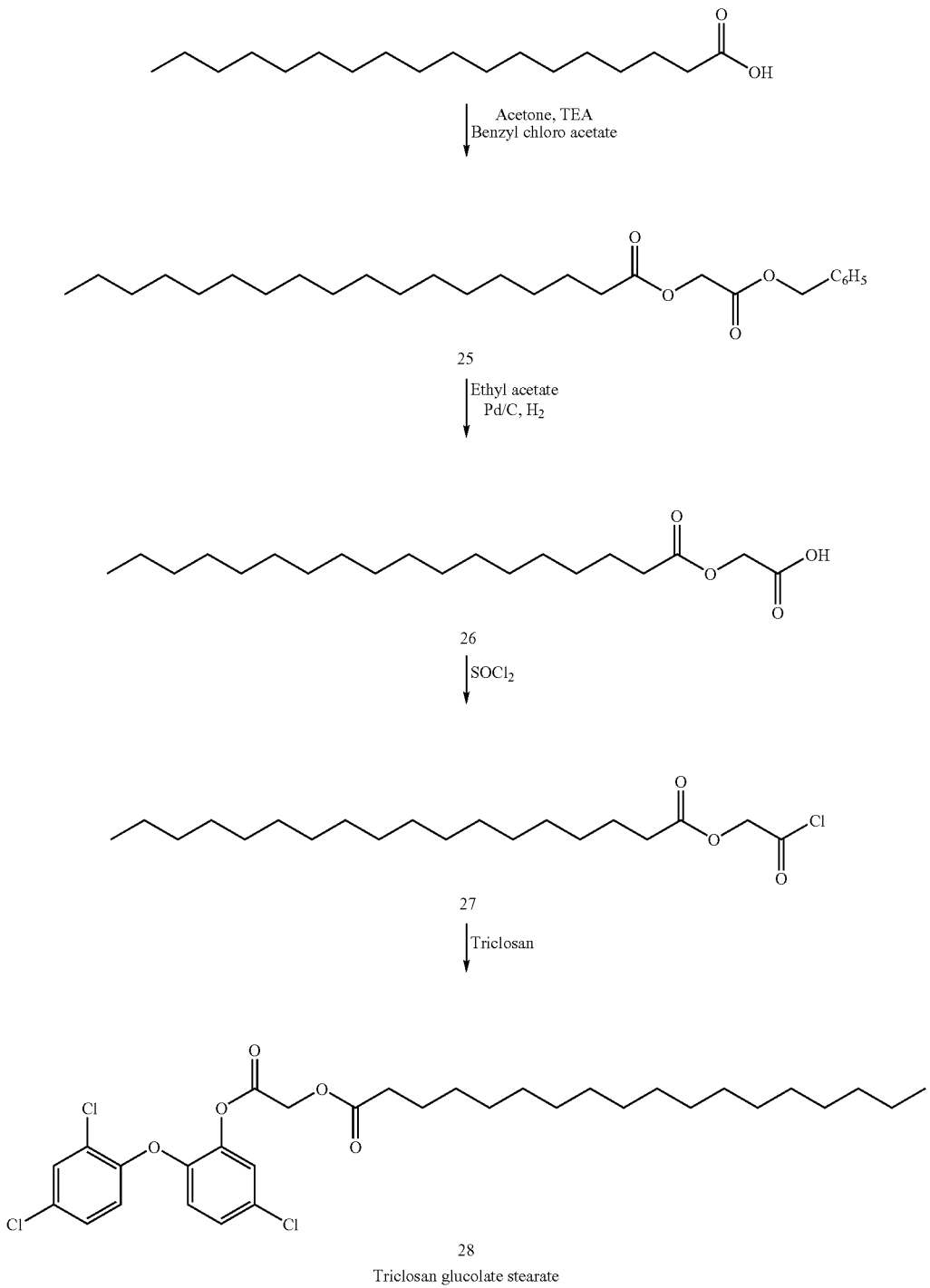

28
Triclosan glucolate stearate

Example 25

Synthesis of Benzyl Glycolate Stearate

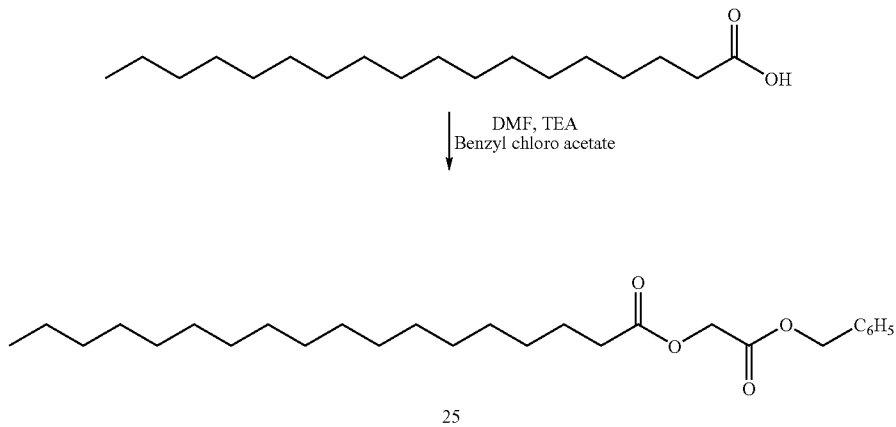

Into a clean and dry 2 liter, 3 necked round bottom flask equipped with a desiccant tube was added 100 grams of stearic acid in 500 ml of dimethylformamide. 100 ml of anhydrous triethylamine was added to this solution and stirred at room temperature for about 10 minutes. To this stirring solution was added dropwise 80 grams of benzylchloroacetate. The flask was left for stirring at room temperature for 24 hours following which the reaction mixture was precipitated in cold water followed by extraction using ethyl acetate. The ethyl acetate layer was washed with 5% solution of sodium bicarbonate followed by drying using sodium sulphate. Ethyl acetate was distilled off using high vacuum distillation to yield 150 grams of crude 25. Crude 25 was purified by column chromatography using hexane as an eluant to yield 92 grams of pure 25 as a low melting white solid.

Example 26

Synthesis of 2-hydroxy acetic acid stearate

Into a hydrogenation apparatus was added 250 grams of 25 dissolved in 500 ml of Ethyl acetate. 2 grams of 10% Palladium on Carbon was added to the solution and the resulting reaction mixture in the pressure vessel was purged with hydrogen maintained at a pressure of 4 kg and stirred for 16 hours. The completion of reaction was determined by disappearance of starting material using thin layer chromatography. The reaction mixture after completion was filtered using the high flow bed and washed with ethyl acetate. Ethyl acetate was distilled off to yield 250 grams of crude 26. The resulting crude product was purified via crystallization using a mixture of ethyl acetate and hexane to yield 185 grams of pure 26 with a melting point of 74-76° C.

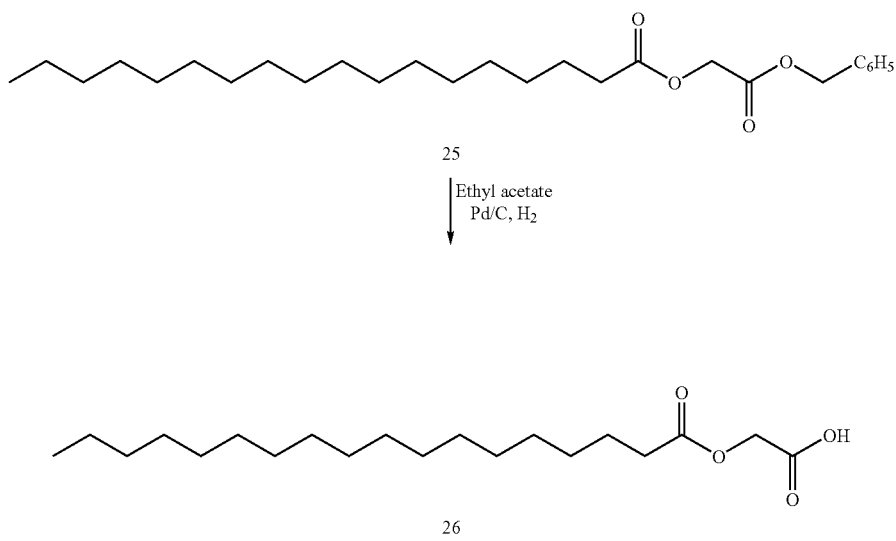

Example 27

Synthesis of Stearic Acid Glycolic Acid Chloride

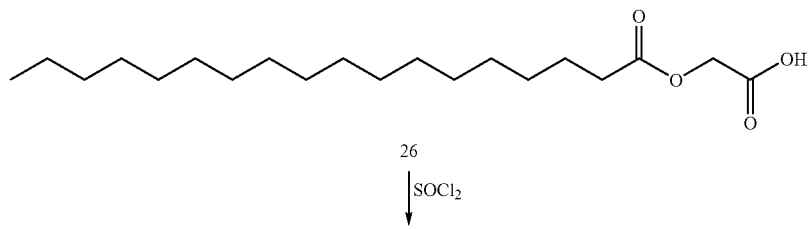

26

↓ SOCl₂

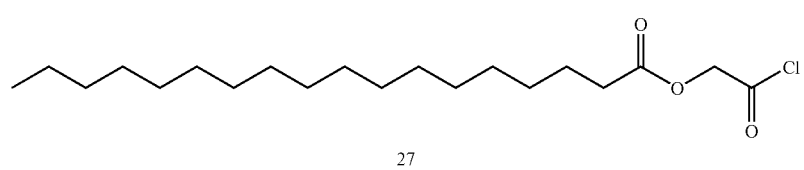

27

A clean and dry 250 ml round bottom flask equipped with a nitrogen inlet was charged with 25 grams of glycolic acid stearate 26 and 30 ml of thionyl chloride. The flask was left for stirring along with refluxing for 24 hours following which thionyl chloride was distilled under vacuum. 60 ml of toluene was added to the reaction mixture and any remaining thionyl chloride was distilled off the reaction mixture along with toluene under high vacuum to yield 24 grams of light yellow colored acid chloride 27, which was used as such in the next synthetic step.

Example 28

Synthesis of Triclosan Glycolic Acid Stearate

Into a clean and dry 1 liter, 3 necked round bottom flask equipped with a nitrogen inlet was added 15 grams of triclosan in 150 ml of ethyl acetate. 15 ml of pyridine was added to the reaction mixture and the reaction mixture was left for stirring at room temperature for 10 minutes. To this stirring solution was added dropwise 24 grams of stearic acid glycolic acid chloride 27 dissolved in 30 ml of ethyl acetate and the reaction was left for stirring at room temperature for twenty four hours following which the triethylamine hydrochloride salt was filtered off and the ethyl acetate layer was washed with 5% solution of sodium bicarbonate followed by drying using sodium sulphate. Ethyl acetate was distilled off using high vacuum distillation to yield 22 grams of crude 28. Complete hydrolytic degradation of 500 mg of triclosan glycolic acid stearate in 50 ml of pH 9.0 at 100° C. occurred in 27 hours.

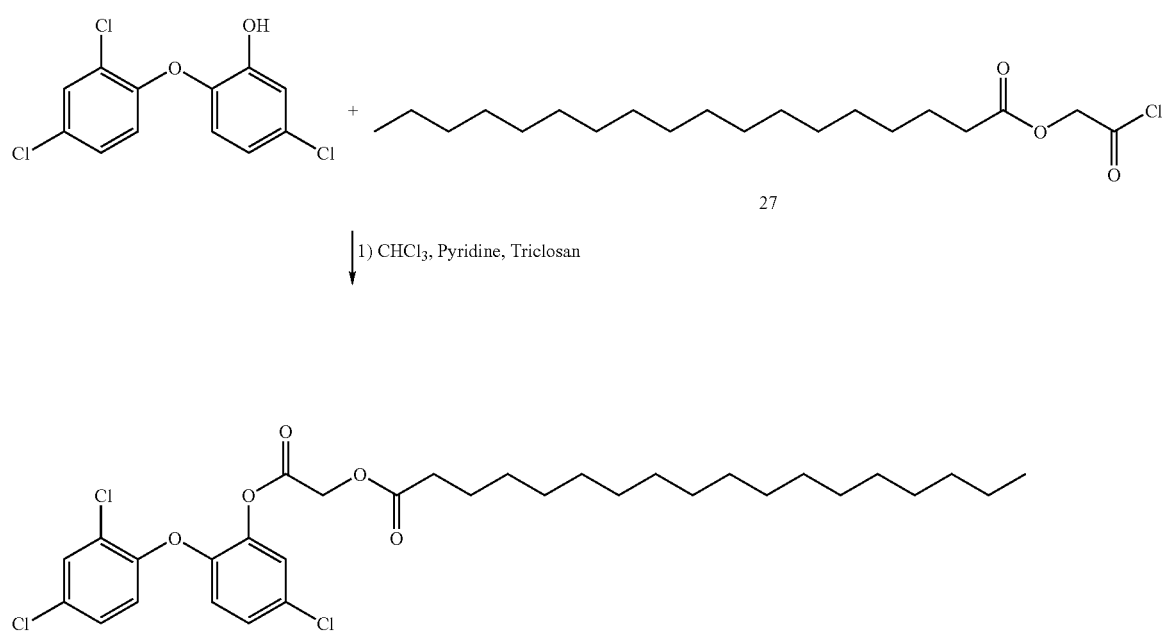

28

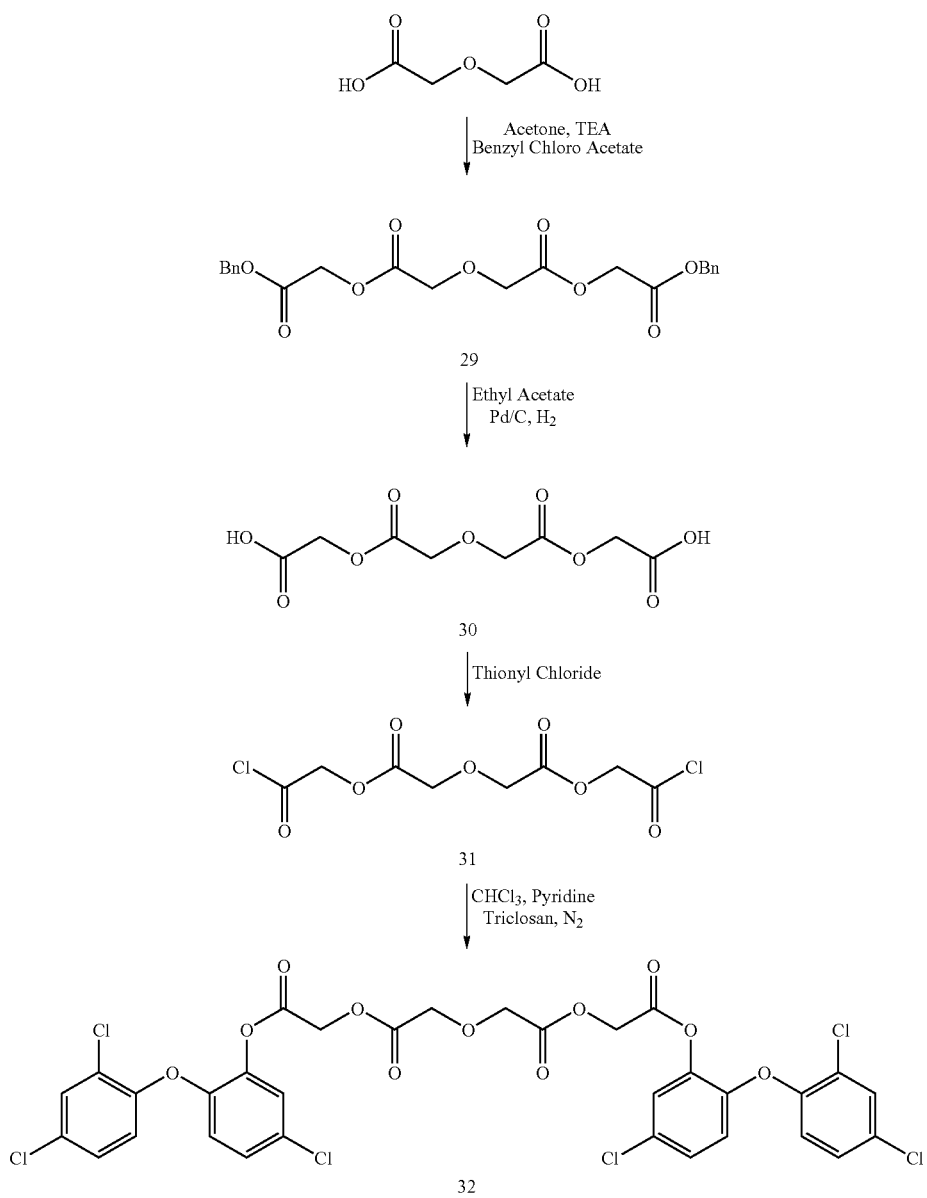

Example 29

Synthesis of Dibenzyl Diglycolyl Diglycolate (a) Synthesis of Benzyl Chloroacetate

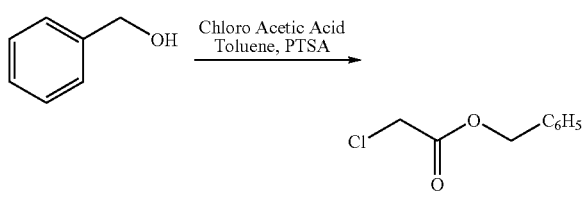

Into a clean and dry 3 liter, 3 necked round bottom flask equipped with a desiccant tube was added 420 grams of benzyl alcohol, 440 grams of chloroacetic acid, 2000 ml of toluene and 10 grams of p-toluene sulphonic acid. The flask was left with stirring in an oil bath maintained at 140° C. for one hour when all the starting material disappeared as determined by thin layer chromatography. The reaction mixture was cooled to room temperature and washed with 5% solution of sodium bicarbonate followed by water. The toluene layer was dried using sodium sulphate and the toluene was distilled off using high vacuum distillation to yield 560 grams of colorless benzylchloroacetate with a purity of 99% as determined by gas chromatography.

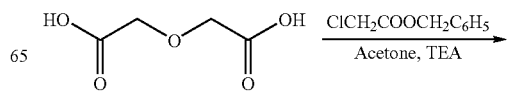

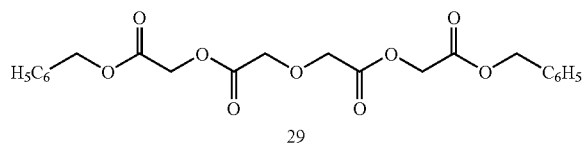

29

(b) Reaction of Diglycolic Acid with Benzyl Chloroacetate

Into a clean and dry 2 liter, 3 necked round bottom flask equipped with a desiccant tube was added 40 grams of diglycolic acid in 200 ml of acetone. 125 ml of anhydrous triethylamine was added to this solution and stirred at room temperature for about 10 minutes. To this stirring solution was added dropwise 127 grams of benzylchloroacetate. The flask was left for stirring at room temperature for 24 hours following which the reaction mixture was precipitated in cold water followed by extraction using ethyl acetate. The ethyl acetate layer was washed with 5% solution of sodium bicarbonate followed by drying using sodium sulphate. Ethyl acetate was distilled off using high vacuum distillation and the compound was precipitated in hexane to yield 108 grams of pure 29 with a melting point of 59-60° C.

Example 30

Synthesis of Diglycolic Acid Diglycolate

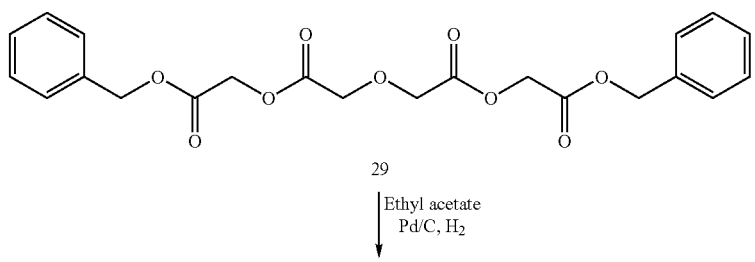

29

| Ethyl acetate
| Pd/C, H$_2$
↓

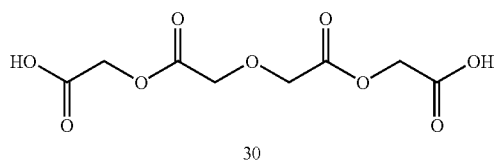

30

Into a hydrogenation apparatus was added 90 grams of 29 dissolved in 250 ml of ethyl acetate. 15 grams of 10% palladium on carbon was added to the solution and the resulting reaction mixture in the pressure vessel was purged with hydrogen maintained at a pressure of 4 kg and stirred for 16 hours. The completion of reaction was determined by disappearance of starting material using thin layer chromatography. The reaction mixture after completion was filtered using the high flow bed and washed with ethyl acetate. Ethyl acetate was distilled off to yield 48 grams of crude 30. The resulting crude product was purified via crystallization using a mixture of ethyl acetate and hexane to yield 35 grams of pure 30 with a melting point of 100-102° C.

Example 31

Synthesis of Diglycolic Acid Diglycolyl Chloride

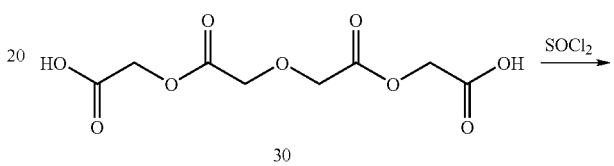

A clean and dry 250 ml round bottom flask equipped with a nitrogen inlet was charged with 30 grams of diglycolic acid diglycolate 30 and 150 ml of thionyl chloride. The flask was left for stirring along with refluxing for 24 hours following which thionyl chloride was distilled under vacuum. 60 ml of toluene was added to the reaction mixture and any remaining thionyl chloride was distilled off the reaction mixture along with toluene under high vacuum to yield 30 grams of light yellow colored acid chloride 31 that was used as such in the next synthetic step.

Example 32

Synthesis of Triclosan Dimer From Diglycolic Acid Diglycolyl Chloride

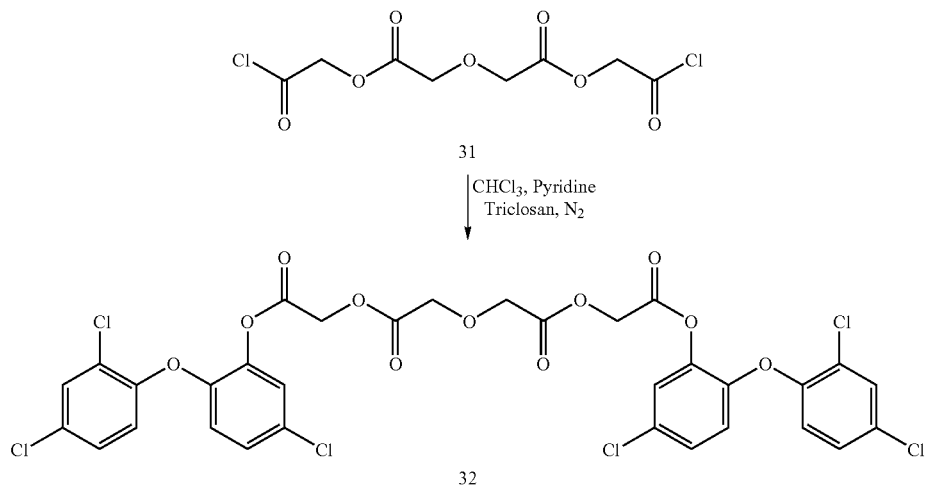

Into a clean and dry 1 liter, 3 necked round bottom flask equipped with a nitrogen inlet was added 31 grams of triclosan in 200 ml of chloroform. 12 ml of pyridine was added to the reaction mixture and the reaction mixture was cooled to 0° C. along with stirring. To this stirring solution was added dropwise 20 grams of diglycolic acid diglycolyl chloride 31 dissolved in 50 ml of chloroform and the reaction was left for stirring at 0° C. for two hours following which the reaction mixture was left for stirring overnight. The reaction mixture was precipitated in cold water. The chloroform layer was washed with 5% solution of sodium bicarbonate followed by drying using sodium sulphate. Chloroform was distilled off using high vacuum distillation and the crude compound was purified using column chromatography to yield 40 grams of light yellow colored syrup of dimer 32 with 92% purity as determined by HPLC.

When any variable occurs more than one time in any constituent or in any formula, its definition in each occurrence is independent of its definition at every other occurrence. Combinations of substituents and/or variables are permissible only if such combinations result in stable compounds.

It is believed the chemical formulas and names used herein correctly and accurately reflect the underlying chemical compounds. However, the nature and value of the present invention does not depend upon the theoretical correctness of these formulae, in whole or in part. Thus it is understood that the formulas used herein, as well as the chemical names attributed to the correspondingly indicated compounds, are not intended to limit the invention in any way, including restricting it to any specific tautomeric form or to any specific optical or geometric isomer, except where such stereochemistry is clearly defined.

When ranges are used herein for physical properties, such as molecular weight, or chemical properties, such as chemical formulae, all combinations and subcombinations of ranges and specific embodiments therein are intended to be included.

The disclosures of each patent, patent application and publication cited or described in this document are hereby incorporated herein by reference, in their entireties.

Those skilled in the art will appreciate that numerous changes and modifications maybe made to the preferred embodiments of the invention and that such changes and modifications maybe made without departing from the spirit of the invention. It is, therefore, intended that the appended claims cover all such equivalent variations as fall within the true spirit and scope of the invention.

What is claimed is:

1. A functionalized triclosan oligomer of formula IX:

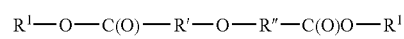

wherein:

R' and R" are each independently R;

R is a diradical derived from $C_{1-25}$ alkyl, aryl, or aryl-$(C_{1-6}alkyl)_{1-3}$-, wherein from 1-4 of the $CH_2$ groups within the alkyl chain are optionally independently replaced by O or S atoms, such that each of said O or S atoms is attached only to carbon atoms in the alkyl chain, with the proviso that multiple heteroatoms must be separated from each other by at least two carbon atoms and from the diradical chain ends by at least one carbon atom; or R is —[$CH_2CH_2O$—]$_p$—, wherein p is an integer from about 10 to about 50; and $R^1$ is:

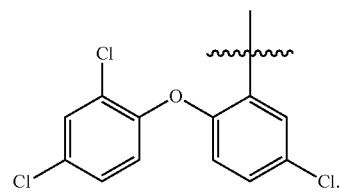

2. A functionalized triclosan oligomer according to claim 1 having the structure:

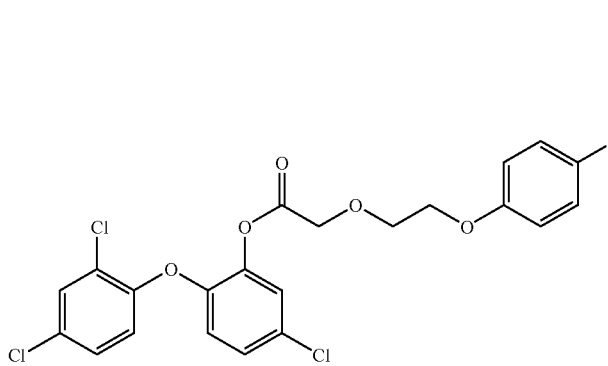
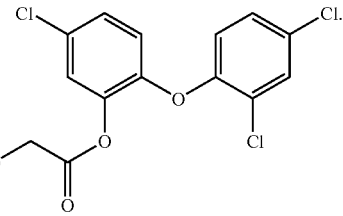

3. A medical device or medical device coating, comprising: a functionalized triclosan oligomer according to claim 1.

4. The medical device or medical device coating according to claim 3, wherein the device or coating is selected from a surgical suture coating, staple coating, orthopedic device coating, fabric coating, surgical mesh coating, clip coating, stent coating, needle coating, catheter, and catheter coating.

5. A composition, comprising a functionalized triclosan oligomer of claim 1, wherein the composition is selected from an oral composition, home care composition, anti-tartar dental product, antimicrobial fabric, antimicrobial flush solution, chewing gum composition, soap composition, toothpaste composition, flowable personal care or cleaning composition, and a pharmaceutical composition.

6. A medical device according to claim 3, wherein the device is implantable.

7. A controlled drug delivery system characterized by at least one polymer composition comprising a functionalized triclosan oligomer according to claim 1, wherein said polymer composition is physically admixed with a biologically or pharmacologically active agent.

8. A functionalized triclosan oligomer according to claim 1 having the structure:

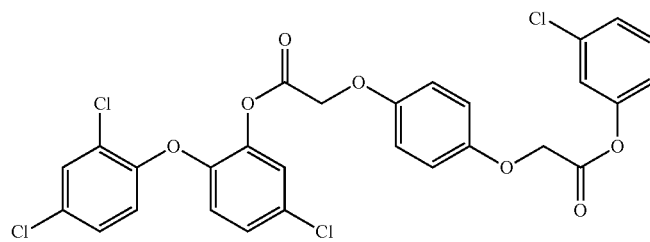

9. A functionalized triclosan oligomer according to claim 1 having the structure:

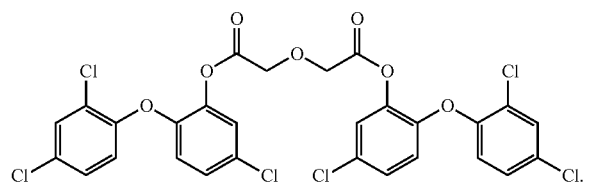

10. A functionalized triclosan oligomer according to claim 1, wherein:

R is independently selected from $C_{2-12}$ alkyl, phenyl, and phenyl-$(C_{1-6}$ alkyl$)_{1-3}$-.

11. A functionalized triclosan oligomer according to claim 1, wherein:
R is $(CH_2)$.

12. A functionalized triclosan oligomer according to claim 1, wherein:
R is $(CH_2)_3$.

13. A functionalized triclosan oligomer according to claim 1, wherein:
R is $(CH_2)_4$.

14. A functionalized triclosan oligomer according to claim 1, wherein:
R is $(CH_2OCH_2)$.

15. A functionalized triclosan oligomer according to claim 1, wherein:
R is $(CH_2CH_2OCH_2CH_2)$.

16. A functionalized triclosan oligomer according to claim 1, wherein:
R is —O—[CH$_2$CH$_2$—O—CH$_2$CH$_2$—O—CH$_2$CH$_2$—O]—.

17. A functionalized triclosan oligomer according to claim 1, wherein
the —O—C(O)—R'—O—R"—C(O)O— group is:

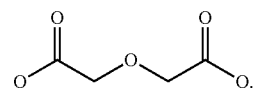

18. A functionalized triclosan oligomer according to claim 1, wherein
the —O—C(O)—R'—O—R"—C(O)O— group is:

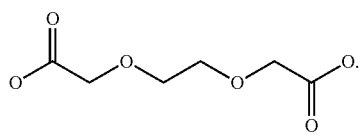

19. A functionalized triclosan oligomer according to claim 1, wherein
the —O—C(O)—R'—O—R"—C(O)O— group is:

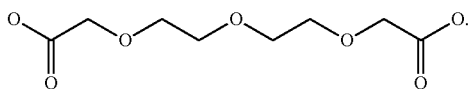

20. A functionalized triclosan oligomer according to claim 1, wherein
the —O—C(O)—R'—O—R"—C(O)O— group is:

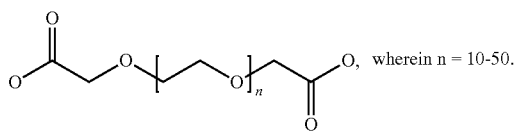, wherein n = 10-50.

21. A functionalized triclosan oligomer according to claim 1, wherein
the —O—C(O)—R'—O—R"—C(O)O— group is:

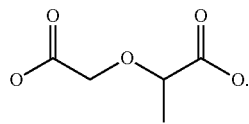

22. A functionalized triclosan oligomer according to claim 1, wherein
the —O—C(O)—R'—O—R"—C(O)O— group is:

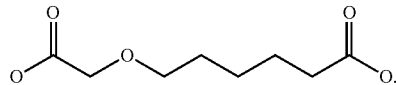

23. A functionalized triclosan oligomer according to claim 1, wherein
the —O—C(O)—R'—O—R"—C(O)O— group is:

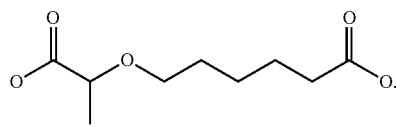

24. A functionalized triclosan oligomer according to claim 1, wherein
the —O—C(O)—R'—O—R"—C(O)O— group is:

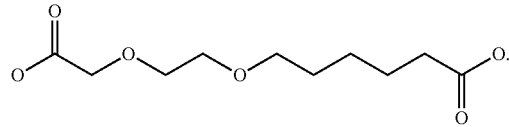

\* \* \* \* \*